United States Patent
Fukushima et al.

(10) Patent No.: US 12,054,660 B2
(45) Date of Patent: Aug. 6, 2024

(54) COMPOUND, COMPOSITION, CURED SUBSTANCE, OPTICALLY ANISOTROPIC BODY, OPTICAL ELEMENT, AND LIGHT GUIDE ELEMENT

(71) Applicant: FUJIFILM Corporation, Tokyo (JP)

(72) Inventors: Yuki Fukushima, Minami-Ashigara (JP); Megumi Okubo, Minami-Ashigara (JP); Keisuke Kodama, Minami-Ashigara (JP); Shunya Katoh, Minami-Ashigara (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 17/847,658

(22) Filed: Jun. 23, 2022

(65) Prior Publication Data

US 2023/0042009 A1 Feb. 9, 2023

(30) Foreign Application Priority Data

Jun. 23, 2021 (JP) ................................. 2021-104476

(51) Int. Cl.
| | | |
|---|---|---|
| *C09K 19/28* | (2006.01) | |
| *C07C 323/12* | (2006.01) | |
| *C07C 323/19* | (2006.01) | |
| *C09K 19/18* | (2006.01) | |
| *C09K 19/32* | (2006.01) | |
| *C09K 19/34* | (2006.01) | |
| *G02B 5/30* | (2006.01) | |
| *G02B 6/27* | (2006.01) | |

(52) U.S. Cl.
CPC ............ *C09K 19/28* (2013.01); *C07C 323/12* (2013.01); *C07C 323/19* (2013.01); *C09K 19/18* (2013.01); *C09K 19/322* (2013.01); *C09K 19/3405* (2013.01); *G02B 5/3016* (2013.01); *G02B 6/2726* (2013.01); *C09K 2323/02* (2020.08)

(58) Field of Classification Search
CPC ...... C09K 19/18; C09K 19/28; C09K 19/322; C09K 19/3405; C09K 2323/02; C07C 323/12; C07C 323/19; G02B 5/3016
USPC ......................................................... 526/257
See application file for complete search history.

(56) References Cited

U.S. PATENT DOCUMENTS

| | | | |
|---|---|---|---|
| 2019/0177268 A1 | 6/2019 | Fukushima et al. | |
| 2021/0002556 A1* | 1/2021 | Goto | ......................... G02B 1/08 |
| 2021/0149098 A1 | 5/2021 | Sasata et al. | |
| 2023/0205044 A1* | 6/2023 | Sato | ......................... G02B 5/18 |
| | | | 349/202 |

FOREIGN PATENT DOCUMENTS

| | | | | |
|---|---|---|---|---|
| WO | WO 2018/034216 A1 | 2/2018 | | |
| WO | WO 2020/022496 A1 | 1/2020 | | |
| WO | WO-2022050321 A1 * | 3/2022 | ............. | G02F 1/292 |

OTHER PUBLICATIONS

Kuehen et al "Highly efficient chirality inducers in nematic liquid crystals", Liquid Crystals, 2019, 46(12), p. 1763-1768 (Year: 2019).*

* cited by examiner

*Primary Examiner* — Ruiyun Zhang
(74) *Attorney, Agent, or Firm* — Birch, Stewart, Kolasch & Birch, LLP

(57) ABSTRACT

A compound represented by the General Formula (I) as defined herein, in which, in the General Formula (I), $P^1$ and $P^2$ each independently represent a hydrogen atom, —CN, —NCS, or a polymerizable group, $Sp^1$ and $Sp^2$ each independently represent a single bond or a divalent linking group as defined herein, $Z^1$, $Z^2$ and $Z^3$ each independently represent a particular linking group as defined herein, $X^1$ and $X^2$ each independently represent a single bond or —S as defined herein, k represents an integer of 2 to 4, m and n each independently represent an integer of 0 to 3 as defined herein, $A^1$, $A^2$, $A^3$, and $A^4$ each independently represent a particular group as defined herein is provided.

20 Claims, No Drawings

COMPOUND, COMPOSITION, CURED SUBSTANCE, OPTICALLY ANISOTROPIC BODY, OPTICAL ELEMENT, AND LIGHT GUIDE ELEMENT

CROSS-REFERENCE TO RELATED APPLICATIONS

This application is based on and claims priority under 35 USC 119 from Japanese Patent Application No. 2021-104476 filed on Jun. 23, 2021, the entire contents of which are incorporated herein by reference.

BACKGROUND OF THE INVENTION

1. Field of the Invention

The present invention relates to a compound, a composition, a cured substance, an optically anisotropic body, an optical element, and a light guide element.

2. Description of the Related Art

A compound having liquid crystallinity (hereinafter, also referred to as a "liquid crystal compound") and a composition having liquid crystallinity (hereinafter, also referred to as a "liquid crystal composition") can be applied to various use applications.

For example, WO2020/022496A describes that diffracted light with high diffraction efficiency can be obtained at a large diffraction angle by an optical element including an optically anisotropic layer consisting of a cured substance of a composition containing a liquid crystal compound. WO2020/022496A describes that good diffraction efficiency can be obtained by using a liquid crystal compound having a high refractive index anisotropy Δn (hereinafter, also simply referred to as "Δn").

In addition, WO2018/034216A discloses a liquid crystal compound having a high Δn. Further, WO2018/034216A discloses a reflective film obtained by curing a composition containing a liquid crystal compound having a high Δn.

SUMMARY OF THE INVENTION

As described in WO2020/022496A and WO2018/034216A, a liquid crystal compound having a high Δn is useful for various use applications. In addition, for example, in a case of being mixed with another compound having liquid crystallinity, a compound having a high Δn can be used to form a liquid crystal composition having a high Δn even in a case where the compound itself does not have liquid crystallinity, which is useful in various use applications.

An object of the present invention is to provide a compound having a high refractive index anisotropy Δn, a composition containing the compound, a cured substance, an optically anisotropic body, an optical element, and a light guide element.

As a result of intensive examination, the inventors of the present invention have found that the above object can be achieved by the following means.

<1> A Compound Represented by the Following General Formula (I).

(I)

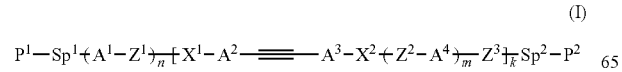

In the General Formula (I), $P^1$ and $P^2$ each independently represent a hydrogen atom, —CN, —NCS, or a polymerizable group, $Sp^1$ and $Sp^2$ each independently represent a single bond or a divalent linking group, $Sp^1$ and $Sp^2$ do not represent a divalent linking group containing at least one group selected from the group consisting of an aromatic hydrocarbon ring group, an aromatic heterocyclic group, and an aliphatic hydrocarbon ring group, $Z^1$, $Z^2$ and $Z^3$ each independently represent a single bond, —O—, —S—, —CHR—, —CHRCHR—, —OCHR—, —CHRO—, —SO—, —SO$_2$—, —COO—, —OCO—, —CO—S—, —S—CO—, —O—CO—O—, —CO—NR—, —NR—CO—, —SCHR—, —CHRS—, —SO—CHR—, —CHR—SO—, —SO$_2$—CHR—, —CHR—SO$_2$—, —CF$_2$O—, —OCF$_2$—, —CF$_2$S—, —SCF$_2$—, —OCHRCHRO—, —SCHRCHRS—, —SO—CHRCHR—SO—, —SO$_2$—CHRCHR—SO$_2$—, —CH=CH—COO—, —CH=CH—OCO—, —COO—CH=CH—, —OCO—CH=CH—, —COO—CHRCHR—, —OCO—CHRCHR—, —CHRCHR—COO—, —CHRCHR—OCO—, —COO—CHR—, —OCO—CHR—, —CHR—COO—, —CHR—OCO—, —CR=CR—, —CR=N—, —N=CR—, —N=N—, —CR=N—N=CR—, —CF=CF—, or —C≡C—;

R represents a hydrogen atom or an alkyl group having 1 to 10 carbon atoms; in a case where a plurality of R's are present, the plurality of R's may be the same or different from each other; in a case where a plurality of Z's and a plurality of $Z^2$'s are present, the plurality of $Z^1$'s and the plurality of $Z^2$'s may be respectively the same or different from each other; a plurality of $Z^3$'s may be the same or different from each other, $Z^3$ linked to $Sp^2$ represents a single bond, $X^1$ and $X^2$ each independently represent a single bond or —S—, a plurality of $X^1$'s and a plurality of $X^2$'s may be respectively the same or different from each other, at least any one of the plurality of $X^1$'s or the plurality of $X^2$'s represents —S—, k represents an integer of 2 to 4, m and n each independently represent an integer of 0 to 3, a plurality of m's may be the same or different from each other, $A^1$, $A^2$, $A^3$, and $A^4$ each independently represent a group represented by any of the following General Formulae (B-1) to (B-7) or a group formed by linking two or three groups represented by any of the General Formulae (B-1) to (B-7), a plurality of $A^2$'s and a plurality of $A^3$'s may be respectively the same or different from each other, and in a case where a plurality of $A^1$'s and a plurality of $A^4$'s are present, the plurality of $A^1$'s and the plurality of $A^4$'s may be respectively the same or different from each other.

(B-1)

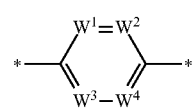

(B-2)

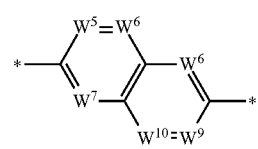

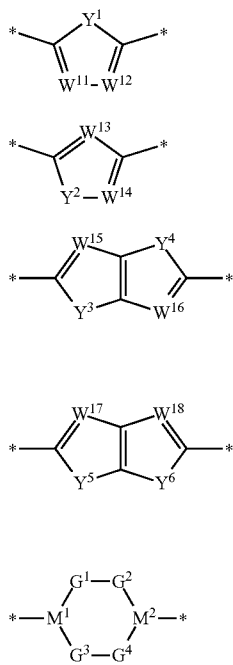

In the General Formulae (B-1) to (B-7), $W^1$ to $W^{18}$ each independently represent $CR^1$ or N, $R^1$ represents a hydrogen atom or the following substituent L, $Y^1$ to $Y^6$ each independently represent $NR^2$, O, or S, $R^2$ represents a hydrogen atom or the following substituent L, $G^1$ to $G^4$ each independently represent $CR^3R^4$, NRS, O, or S, $R^3$ to $R^5$ each independently represent a hydrogen atom or the following substituent L, $M^1$ and $M^2$ each independently represent $CR^6$ or N, $R^6$ represents a hydrogen atom or the following substituent L,

* represents a bonding position, and the substituent L is an alkyl group having 1 to 10 carbon atoms, an alkoxy group having 1 to 10 carbon atoms, an alkylamino group having 1 to 10 carbon atoms, an alkylthio group having 1 to 10 carbon atoms, an alkanoyl group having 1 to 10 carbon atoms, an alkanoyloxy group having 1 to 10 carbon atoms, an alkanoylamino group having 1 to 10 carbon atoms, an alkanoylthio group having 1 to 10 carbon atoms, an alkyloxycarbonyl group having 2 to 10 carbon atoms, an alkylaminocarbonyl group having 2 to 10 carbon atoms, an alkylthiocarbonyl group having 2 to 10 carbon atoms, a hydroxy group, an amino group, a mercapto group, a carboxy group, a sulfo group, an amide group, a cyano group, a nitro group, a halogen atom, or a polymerizable group; in a case where the above group described as the substituent L has —$CH_2$—, a group formed by replacing at least one of —$CH_2$— contained in the above group with —O—, —CO—, —CH=CH—, or —C≡C— is also included in the substituent L; and in a case where the above group described as the substituent L has a hydrogen atom, a group formed by replacing at least one of hydrogen atoms contained in the above group with at least one selected from the group consisting of a fluorine atom and a polymerizable group is also included in the substituent L.

<2> The compound according to <1>, in which n and m in the General Formula (I) represent 0.

<3> The compound according to <1> or <2>, in which k in the General Formula (I) represents 2.

<4> The compound according to any one of <1> to <3>, in which at least two of the plurality of $X^1$'s and the plurality of $X^2$'s in the General Formula (I) represent —S—.

<5> The compound according to <1>, in which in the General Formula (I), n represents 0; m represents 0 or 1, m at a position closest to $Sp^2$ represents 0; in a case where $X^1$ linked to $Sp^1$ is denoted by $X^{1A}$ and $X^2$ linked to $Z^3$ linked to $Sp^2$ is denoted by $X^{2A}$, at least one of $X^{1A}$ or $X^{2A}$ represents —S—, $X^1$ other than $X^{1A}$ and $X^2$ other than $X^{2A}$ represent a single bond; $Z^2$ and $Z^3$ each independently represent a single bond, —O—, —CHR—, —CHRCHR—, —OCHR—, —CHRO—, —SO—, —$SO_2$—, —COO—, —OCO—, —CO—S—, —S—CO—, —O—CO—O—, —CO—NR—, —NR—CO—, —SO—CHR—, —CHR—SO—, —$SO_2$—CHR—, —CHR—$SO_2$—, —$CF_2$O—, —$OCF_2$—, —OCHRCHRO—, —SO—CHRCHR—SO—, —$SO_2$—CHRCHR—$SO_2$—, —CH=CH—COO—, —CH=CH—OCO—, —COO—CH=CH—, —OCO—CH=CH—, —COO—CHRCHR—, —OCO—CHRCHR—, —CHRCHR—COO—, —CHRCHR—OCO—, —COO—CHR—, —OCO—CHR—, —CHR—COO—, —CHR—OCO—, —CR=CR—, —CR=N—, —N=CR—, —N=N—, —CR=N—N=CR—, —CF=CF—, or —C≡C—, $Z^3$ linked to $Sp^2$ represents a single bond; R represents a hydrogen atom or an alkyl group having 1 to 10 carbon atoms; and in a case where a plurality of R's are present, the plurality of R's may be the same or different from each other.

<6> The compound according to any one of <1> to <5>, in which at least one of $P^1$ or $P^2$ in the General Formula (I) represents a polymerizable group.

<7> The compound according to any one of <1> to <6>, in which in the General Formula (I), $P^1$ represents a polymerizable group, n represents 0, and $X^1$ linked to $Sp^1$ represents —S—.

<8> The compound according to any one of <1> to <7>, in which $A^1$, $A^2$, $A^3$, and $A^4$ in the General Formula (I) each independently represent a group represented by the General Formula (B-1) or (B-2), $W^1$ and $W^2$ in the General Formula (B-1) do not represent N at the same time, $W^3$ and $W^4$ do not represent N at the same time, $W^5$ and $W^6$ in the General Formula (B-2) do not represent N at the same time, and $W^9$ and $W^{10}$ do not represent N at the same time.

<9> The compound according to any one of <1> to <8>, in which at least one of $A^1$, $A^2$, $A^3$, or $A^4$ in the General Formula (I) has the substituent L.

<10> The compound according to any one of <1> to <9>, in which $Z^1$, $Z^2$, and $Z^3$ in the General Formula (I) each independently represent a single bond, —CHR—, —CHRCHR—, —OCHR—, —CHRO—, or —OCHRCHRO—, $Z^3$ linked to $Sp^2$ represents a single bond; R represents a hydrogen atom or an alkyl group having 1 to 10 carbon atoms; and in a case where a plurality of R's are present, the plurality of R's may be the same or different from each other.

<11> The compound according to <1>, in which the compound represented by the General Formula (I) is a compound represented by the following General Formula (I-2) or (I-3).

(I-2)

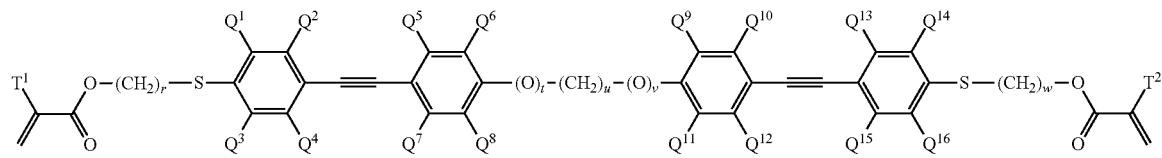

(I-3)

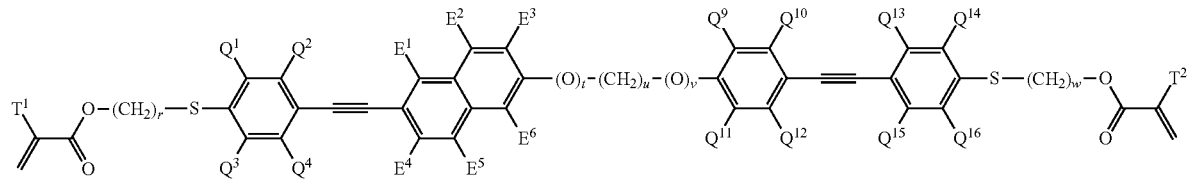

In the General Formulae (I-2) and (I-3), $T^1$ and $T^2$ each independently represent a hydrogen atom or a methyl group, r represents an integer of 1 to 5, t and v each independently represent 0 or 1, u represents 1 or 2, w represents an integer of 1 to 5, $Q^1$ to $Q^{16}$ each independently represent a hydrogen atom or the substituent L, and $E^1$ to $E^6$ each independently represent a hydrogen atom or the substituent L.

<12> The compound according to any one of <1> to <11>, in which the compound has liquid crystallinity.

<13> A composition comprising the compound according to any one of <1> to <12>.

<14> The composition according to <13>, further comprising a polymerization initiator.

<15> The composition according to <13> or <14>, further comprising a chiral agent.

<16> The composition according to any one of <13> to <15>, in which the composition has liquid crystallinity.

<17> The composition according to any one of <13> to <16>, in which the composition is used for forming an optically anisotropic layer.

<18> A cured substance that is obtained by curing the composition according to any one of <13> to <16>.

<19> An optically anisotropic body that is obtained by curing the composition according to any one of <13> to <16>.

<20> An optical element comprising an optically anisotropic layer formed from the composition according to any one of <13> to <16>, in which the optically anisotropic layer has an alignment pattern, and the alignment pattern is an alignment pattern in which an orientation of an optical axis, derived from a compound contained in the composition, continuously changes rotationally along at least one in-plane direction.

<21> A light guide element comprising the optical element according to <20> and a light guide plate.

According to the present invention, it is possible to provide a compound having a high refractive index anisotropy Δn, a composition containing the compound, a cured substance, an optically anisotropic body, an optical element, and a light guide element.

DESCRIPTION OF THE PREFERRED EMBODIMENTS

Hereinafter, embodiments of the present invention will be specifically described, but the present invention is not limited thereto. In the present specification, in a case where numerical values represent a value of physical properties, a value of characteristics, and the like, the description of "(numerical value 1) to (numerical value 2)" means "(numerical value 1) or more and (numerical value 2) or less". In addition, in the present specification, the description of "(meth)acrylate" means "at least any one of acrylate or methacrylate". The same applies to "(meth)acrylic acid", "(meth)acryloyl", "(meth)acrylamide", "(meth)acryloyloxy", and the like.

Compound represented by General Formula (I)

A compound represented by the following General Formula (I) will be described.

(I)

In the General Formula (I), $P^1$ and $P^2$ each independently represent a hydrogen atom, —CN, —NCS, or a polymerizable group. $Sp^1$ and $Sp^2$ each independently represent a single bond or a divalent linking group. However, $Sp^1$ and $Sp^2$ do not represent a divalent linking group containing at least one group selected from the group consisting of an aromatic hydrocarbon ring group, an aromatic heterocyclic group, and an aliphatic hydrocarbon ring group. $Z^1$, $Z^2$ and $Z^3$ each independently represent a single bond, —O—, —S—, —CHR—, —CHRCHR—, —OCHR—, —CHRO—, —SO—, —SO$_2$—, —COO—, —OCO—, —CO—S—, —S—CO—, —O—CO—O—, —CO—NR—, —NR—CO—, —SCHR—, —CHRS—, —SO—CHR—, —CHR—SO—, —SO$_2$—CHR—, —CHR—SO₂—, —CF₂O—, —OCF₂—, —CF₂S—, —SCF₂—, —OCHRCHRO—, —SCHRCHRS—, —SO—CHRCHR—SO—, —SO₂—CHRCHR—SO₂—, —CH=CH—COO—, —CH=CH—OCO—, —COO—CH=CH—, —OCO—CH=CH—, —COO—CHRCHR—, —OCO—CHRCHR—, —CHRCHR—COO—, —CHRCHR—OCO—, —COO—CHR—, —OCO—CHR—, —CHR—COO—, —CHR—OCO—, —CR=CR—, —CR=N—, —N=CR—, —N=N—, —CR=N—N=CR—, —CF=CF—, or —C≡C—. R represents a hydrogen atom or an alkyl group having 1 to 10 carbon atoms, and in a case where a plurality of R's are present, the plurality of R's may be the same or different from each other. In a case where a plurality of $Z^1$'s and a plurality of $Z^2$'s are present, the plurality of $Z^1$'s and the plurality of $Z^2$'s may be respectively the same or different from each other. A plurality of $Z^3$'s may be the same or different from each other, provided that $Z^3$ linked to $Sp^2$ represents a single bond. $X^1$ and $X^2$ each independently represent a single bond or —S—. A plurality of $X^1$'s and a plurality of $X^2$'s may be respectively the same or different from each other. However, at least any one of the plurality of $X^1$'s or the plurality of $X^2$'s represents —S—. k represents an integer of 2 to 4. m and n each independently represent an integer of 0 to 3. A plurality of m's may be the same or different from each other. $A^1$, $A^2$, $A^3$, and $A^4$ each independently represent a group represented by any of the following General Formulae (B-1) to (B-7) or a group formed by linking two or three groups represented by any of the General Formulae (B-1) to (B-7). A plurality of $A^2$'s and a plurality of $A^3$'s may be respectively the same or different from each other; and in a case where a plurality of $A^1$'s and a plurality of $A^4$'s are present, the plurality of $A^1$'s and the plurality of $A^4$'s may be respectively the same or different from each other.

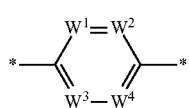 (B-1)

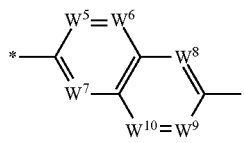 (B-2)

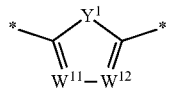 (B-3)

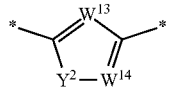 (B-4)

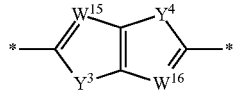 (B-5)

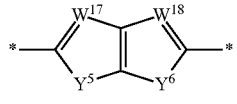 (B-6)

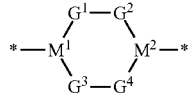 (B-7)

In the General Formulae (B-1) to (B-7), $W^1$ to $W^{18}$ each independently represent $CR^1$ or N, $R^1$ represents a hydrogen atom or the following substituent L, $Y^1$ to $Y^6$ each independently represent $NR^2$, O, or S, $R^2$ represents a hydrogen atom or the following substituent L, $G^1$ to $G^4$ each independently represent $CR^3R^4$, NRS, O, or S, $R^3$ to $R^5$ each independently represent a hydrogen atom or the following substituent L, $M^1$ and $M^2$ each independently represent $CR^6$ or N, $R^6$ represents a hydrogen atom or the following substituent L,

* represents a bonding position, and the substituent L is an alkyl group having 1 to 10 carbon atoms, an alkoxy group having 1 to 10 carbon atoms, an alkylamino group having 1 to 10 carbon atoms, an alkylthio group having 1 to 10 carbon atoms, an alkanoyl group having 1 to 10 carbon atoms, an alkanoyloxy group having 1 to 10 carbon atoms, an alkanoylamino group having 1 to 10 carbon atoms, an alkanoylthio group having 1 to 10 carbon atoms, an alkyloxycarbonyl group having 2 to 10 carbon atoms, an alkylaminocarbonyl group having 2 to 10 carbon atoms, an alkylthiocarbonyl group having 2 to 10 carbon atoms, a hydroxy group, an amino group, a mercapto group, a carboxy group, a sulfo group, an amide group, a cyano group, a nitro group, a halogen atom, or a polymerizable group. However, in a case where the above group described as the substituent L has —CH₂—, a group formed by replacing at least one of —CH₂— contained in the above group with —O—, —CO—, —CH=CH—, or —C≡C— is also included in the substituent L; and in a case where the above group described as the substituent L has a hydrogen atom, a group formed by replacing at least one of hydrogen atoms contained in the above group with at least one selected from the group consisting of a fluorine atom and a polymerizable group is also included in the substituent L.

In the General Formula (I), n represents an integer of 0 to 3, preferably an integer of 0 to 2, more preferably 0 or 1, and still more preferably 0.

In the General Formula (I), m represents an integer of 0 to 3, preferably an integer of 0 to 2, more preferably 0 or 1, and still more preferably 0.

It is particularly preferable that n and m in the General Formula (I) represent 0. In a case where n and m represent 0, the solubility of the compound represented by the General Formula (I) becomes high, which is preferable.

In the General Formula (I), k represents an integer of 2 to 4, preferably 2 or 3, and more preferably 2. In a case where k represents 2, the solubility of the compound represented by the General Formula (I) becomes high, which is preferable.

In the General Formula (I), $P^1$ and $P^2$ each independently represent a hydrogen atom, —CN, —NCS, or a polymerizable group.

Due to the reason that in a case where an optically anisotropic layer is produced from a composition containing a compound represented by the General Formula (I), the alignment state of the compound represented by the General Formula (I) can be fixed, or the durability of the optically anisotropic layer can be improved, it is preferable that at least any one of $P^1$ or $P^2$ represents a polymerizable group.

Due to the reason that the reactivity is more excellent, it is more preferable that both $P^1$ and $P^2$ represent a polymerizable group.

The polymerizable group is not particularly limited, and examples thereof include a known polymerizable group. From the viewpoint of reactivity, a functional group that can be subjected to an addition polymerization reaction is preferable, and a polymerizable ethylenically unsaturated group or a cyclic polymerizable group is more preferable. Examples of the polymerizable group include a (meth) acryloyloxy group, a vinyl group, a maleimide group, a styryl group, an allyl group, an epoxy group, an oxetane group, and a group containing this group. A hydrogen atom in each of the above groups may be substituted with another substituent such as a halogen atom.

Suitable specific examples of the polymerizable group include a group represented by any of Formulae (P-1) to (P-19) below. In the following formulae, * represents a bonding position, Me represents a methyl group, and Et represents an ethyl group.

The polymerizable group is preferably a (meth)acryloyloxy group.

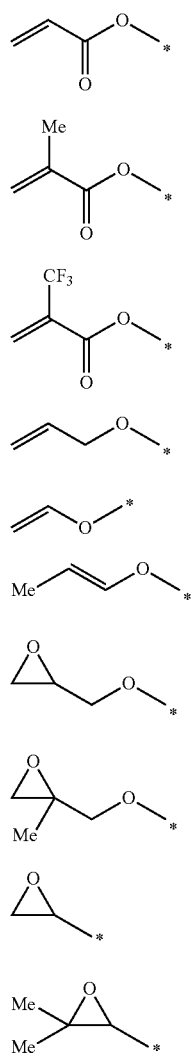

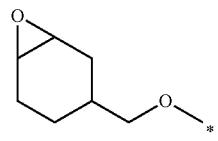

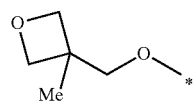

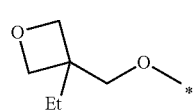

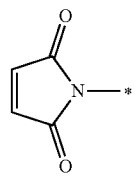

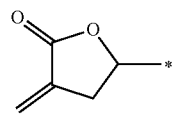

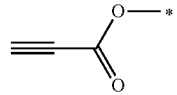

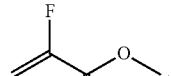

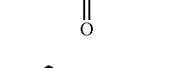

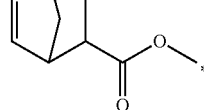

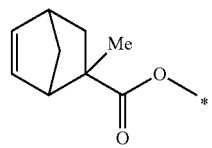

In the General Formula (I), $Sp^1$ and $Sp^2$ each independently represent a single bond or a divalent linking group. However, $Sp^1$ and $Sp^2$ do not represent a divalent linking group containing at least one group selected from the group consisting of an aromatic hydrocarbon ring group, an aromatic heterocyclic group, and an aliphatic hydrocarbon ring group.

The divalent linking group in a case where $Sp^1$ and $Sp^2$ represent a divalent linking group is not particularly limited; however, it is preferable that an alkylene group (preferably an alkylene group having 1 to 20 carbon atoms), an alkenylene group (preferably an alkenylene group having 2 to 20 carbon atoms), —O—, —S—, —CO—, —SO—, —SO₂—, —COO—, —OCO—, —CO—S—, —S—CO—, —O—CO—O—, or a divalent linking group obtained by combining a plurality of these.

It is preferable that $Sp^1$ and $Sp^2$ each independently represent a single bond, or an alkylene group having 1 to 10 carbon atoms, —O—, —CO—, —COO—, —OCO—, or a divalent linking group obtained by combining a plurality of these.

It is more preferable that $Sp^1$ and $Sp^2$ each independently represent a single bond or an alkylene group having 1 to 6 carbon atoms, and it is still more preferable that they represent a single bond or an alkylene group having 1 to 4 carbon atoms.

In the General Formula (I), $Z^1$, $Z^2$ and $Z^3$ each independently represent a single bond, —O—, —S—, —CHR—, —CHRCHR—, —OCHR—, —CHRO—, —SO—, —$SO_2$—, —COO—, —OCO—, —CO—S—, —S—CO—, —O—CO—O—, —CO—NR—, —NR—CO—, —SCHR—, —CHRS—, —SO—CHR—, —CHR—SO—, —$SO_2$—CHR—, —CHR—$SO_2$—, —$CF_2$O—, —$OCF_2$—, —$CF_2$S—, —$SCF_2$—, —OCHRCHRO—, —SCHRCHRS—, —SO—CHRCHR—SO—, —$SO_2$—CHRCHR—$SO_2$—, —CH═CH—COO—, —CH═CH—OCO—, —COO—CH═CH—, —OCO—CH═CH—, —COO—CHRCHR—, —OCO—CHRCHR—, —CHRCHR—COO—, —CHRCHR—OCO—, —COO—CHR—, —OCO—CHR—, —CHR—COO—, —CHR—OCO—, —CR═CR—, —CR═N—, —N═CR—, —N═N—, —CR═N—N═CR—, —CF═CF—, or —C≡C—. R represents a hydrogen atom or an alkyl group having 1 to 10 carbon atoms. In a case where a plurality of R's are present, the plurality of R's may be the same or different from each other. In a case where a plurality of $Z^1$'s and a plurality of $Z^2$'s are present, the plurality of $Z^1$'s and the plurality of $Z^2$'s may be respectively the same or different from each other. A plurality of $Z^3$'s may be the same or different from each other. However, $Z^3$ linked to $Sp^2$ represents a single bond.

$Z^3$ other than the $Z^3$ linked to $Z^1$, $Z^2$, and $Sp^2$ preferably represents a group other than a single bond.

R represents a hydrogen atom or an alkyl group having 1 to 10 carbon atoms, preferably represents a hydrogen atom or an alkyl group having 1 to 6 carbon atoms, more preferably represents a hydrogen atom or an alkyl group having 1 to 4 carbon atoms, and still more preferably represent a hydrogen atom.

In the General Formula (I), $X^1$ and $X^2$ each independently represent a single bond or —S—. A plurality of X's and a plurality of $X^2$'s may be respectively the same or different from each other. However, at least any one of the plurality of $X^1$'s or the plurality of $X^2$'s represents —S—.

In a case where a sulfur atom having a large refractive index is introduced, the Δn of the compound represented by the General Formula (I) can be increased, and thus it is preferable that at least two of the plurality of $X^1$'s and the plurality of $X^2$'s represents —S—.

Due to the reason that the compound represented by the General Formula (I) can become a compound having liquid crystallinity, it is preferable that in the General Formula (I), n represents 0; m represents 0 or 1, m at a position closest to $Sp^2$ represents 0; in a case where $X^1$ linked to $Sp^1$ is denoted by $X^{1A}$ and $X^2$ linked to $Z^3$ linked to $Sp^2$ is denoted by $X^{2A}$, at least one of $X^{1A}$ or $X^{2A}$ represents —S—, $X^1$ other than $X^{1A}$ and $X^2$ other than $X^{2A}$ represent a single bond; and $Z^2$ and $Z^3$ each independently represent a single bond, —O—, —CHR—, —CHRCHR—, —OCHR—, —CHRO—, —SO—, —$SO_2$—, —COO—, —OCO—, —CO—S—, —S—CO—, —O—CO—O—, —CO—NR—, —NR—CO—, —SO—CHR—, —CHR—SO—, —$SO_2$—CHR—, —CHR—$SO_2$—, —$CF_2$O—, —$OCF_2$—, —OCHRCHRO—, —SO—CHRCHR—SO—, —$SO_2$—CHRCHR—$SO_2$—, —CH═CH—COO—, —CH═CH—OCO—, —COO—CH═CH—, —OCO—CH═CH—, —COO—CHRCHR—, —OCO—CHRCHR—, —CHRCHR—COO—, —CHRCHR—OCO—, —COO—CHR—, —OCO—CHR—, —CHR—COO—, —CHR—OCO—, —CR═CR—, —CR═N—, —N═CR—, —N═N—, —CR═N—N═CR—, —CF═CF—, or —C≡C—. However, $Z^3$ linked to $Sp^2$ represents a single bond. The definition and the preferred range of R are as described above. $Z^3$ other than the $Z^3$ linked to $Z^2$ and $Sp^2$ preferably represents a group other than a single bond.

It is more preferable that in the General Formula (I), n and m represents 0, in a case where $X^1$ linked to $Sp^1$ is denoted by $X^{1A}$ and $X^2$ linked to $Z^3$ linked to $Sp^2$ is denoted by $X^{2A}$, at least one of $X^{1A}$ or $X^{2A}$ represents —S—, $X^1$ other than $X^{1A}$ and $X^2$ other than $X^{2A}$ represent a single bond, $Z^3$ represents —O—, —CHR—, —CHRCHR—, —OCHR—, —CHRO—, —SO—, —$SO_2$—, —COO—, —OCO—, —CO—S—, —S—CO—, —O—CO—O—, —CO—NR—, —NR—CO—, —SO—CHR—, —CHR—SO—, —$SO_2$—CHR—, —CHR—$SO_2$—, —$CF_2$—, —$OCF_2$—, —OCHRCHRO—, —SO—CHRCHR—SO—, —$SO_2$—CHRCHR—$SO_2$—, —CH═CH—COO—, —CH═CH—OCO—, —COO—CH═CH—, —OCO—CH═CH—, —COO—CHRCHR—, —OCO—CHRCHR—, —CHRCHR—COO—, —CHRCHR—OCO—, —COO—CHR—, —OCO—CHR—, —CHR—COO—, —CHR—OCO—, —CR═CR—, —CR═N—, —N═CR—, —N═N—, —CR═N—N═CR—, —CF═CF—, or —C≡C—. However, $Z^3$ linked to $Sp^2$ represents a single bond. The definition and the preferred range of R are as described above. $Z^3$ other than the $Z^3$ linked to $Sp^2$ preferably represents a group other than a single bond.

Further, it is also preferable that in the General Formula (I), $P^1$ represents a polymerizable group, n represents 0, and $X^1$ linked to $Sp^1$ represents —S—.

It is preferable that $Z^1$, $Z^2$, and $Z^3$ in the General Formula (I) each independently represent a single bond, —CHR—, —CHRCHR—, —OCHR—, —CHRO—, or —OCHRCHRO—. However, $Z^3$ linked to $Sp^2$ represents a single bond. The definition and the preferred range of R are as described above. $Z^3$ other than the $Z^3$ linked to $Z^1$, $Z^2$, and $Sp^2$ preferably represents a group other than a single bond.

$A^1$, $A^2$, $A^3$, and $A^4$ in the General Formula (I) each independently represent a group represented by any of the following General Formulae (B-1) to (B-7) or a group formed by linking two or three groups represented by any of the General Formulae (B-1) to (B-7). A plurality of $A^2$'s and a plurality of $A^3$'s may be respectively the same or different from each other. In a case where a plurality of $A^1$'s and a plurality of $A^4$'s are present, the plurality of $A^1$'s and the plurality of $A^4$'s may be respectively the same or different from each other.

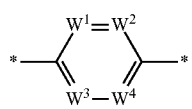

(B-1)

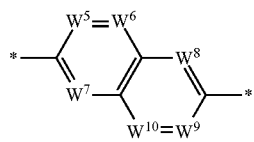

(B-2)

-continued

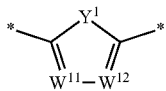
(B-3)

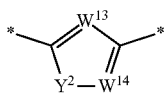
(B-4)

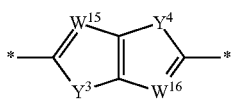
(B-5)

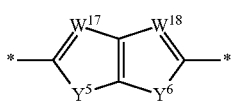
(B-6)

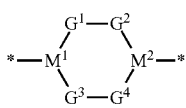
(B-7)

In the General Formulae (B-1) to (B-7), $W^1$ to $W^{18}$ each independently represent $CR^1$ or N, where $R^1$ represents a hydrogen atom or the following substituent L, $Y^1$ to $Y^6$ each independently represent $NR^2$, O, or S, where $R^2$ represents a hydrogen atom or the following substituent L, $G^1$ to $G^4$ each independently represent $CR^3R^4$, NRS, O, or S, where $R^3$ to $R^5$ each independently represent a hydrogen atom or the following substituent L, $M^1$ and $M^2$ each independently represent $CR^6$ or N, where $R^6$ represents a hydrogen atom or the following substituent L, and

* represents a bonding position.

The substituent L is an alkyl group having 1 to 10 carbon atoms, an alkoxy group having 1 to 10 carbon atoms, an alkylamino group having 1 to 10 carbon atoms, an alkylthio group having 1 to 10 carbon atoms, an alkanoyl group having 1 to 10 carbon atoms, an alkanoyloxy group having 1 to 10 carbon atoms, an alkanoylamino group having 1 to 10 carbon atoms, an alkanoylthio group having 1 to 10 carbon atoms, an alkyloxycarbonyl group having 2 to 10 carbon atoms, an alkylaminocarbonyl group having 2 to 10 carbon atoms, an alkylthiocarbonyl group having 2 to 10 carbon atoms, a hydroxy group, an amino group, a mercapto group, a carboxy group, a sulfo group, an amide group, a cyano group, a nitro group, a halogen atom, or a polymerizable group. However, in a case where the above group described as the substituent L has —$CH_2$—, a group formed by replacing at least one —$CH_2$— contained in the above group with —O—, —CO—, —CH=CH—, or —C≡C— is also included in the substituent L. For example, in a case where the above group has two or more —$CH_2$—'s, one —$CH_2$— may be replaced with —O—, and one —$CH_2$— adjacent thereto may be replaced with —CO—, thereby forming an ester group (—O—CO—). In addition, in a case where the above group described as the substituent L has a hydrogen atom, a group formed by replacing at least one of hydrogen atoms contained in the above group with at least one selected from the group consisting of a fluorine atom and a polymerizable group is also included in the substituent L. The above-described polymerizable group is the same as the polymerizable group in a case where $P^1$ and $P^2$ represent a polymerizable group as described above.

In the General Formulae (B-1) to (B-7), $W^1$ to $W^{18}$ each independently represent $CR^1$ or N, and preferably represent $CR^1$.

In a case where a plurality of $R^1$'s are present in General Formulae (B-1) to (B-7), the plurality of $R^1$'s may be the same or different from each other.

$Y^1$ to $Y^6$ each independently represent $NR^2$, O, or S, and preferably represent S.

In a case where a plurality of $R^2$'s are present in the General Formulae (B-5) and (B-6), the plurality of $R^2$'s may be the same or different from each other.

$G^1$ to $G^4$ each independently represent $CR^3R^4$, NRS, O, or S, and preferably represent $CR^3R^4$.

In a case where a plurality of $R^3$'s, a plurality of $R^4$'s, and a plurality of $R^5$'s are present in General Formula (B-7), the plurality of $R^3$'s, the plurality of $R^4$'s, and the plurality of $R^5$'s may be respectively the same or different from each other.

$M^1$ and $M^2$ each independently represent $CR^6$ or N, and preferably represent $CR^6$.

In a case where a plurality of $R^6$'s are present in General Formula (B-7), the plurality of $R^6$'s may be the same or different from each other.

$R^1$ to $R^6$ each independently represent a hydrogen atom or the substituent L described above.

The substituent L is preferably an alkyl group having 1 to 10 carbon atoms, an alkoxy group having 1 to 10 carbon atoms, an alkanoyl group having 1 to 10 carbon atoms, an alkanoyloxy group having 1 to 10 carbon atoms, an alkyloxycarbonyl group having 2 to 10 carbon atoms, a trifluoromethyl group, a hydroxy group, a carboxy group, a cyano group, a nitro group, or a halogen atom.

The substituent L is more preferably an alkyl group having 1 to 10 carbon atoms, an alkoxy group having 1 to 10 carbon atoms, an alkanoyl group having 2 to 10 carbon atoms, an alkanoyloxy group having 2 to 10 carbon atoms, an alkyloxycarbonyl group having 2 to 10 carbon atoms, a trifluoromethyl group, or a halogen atom.

The substituent L is still more preferably an alkyl group having 1 to 6 carbon atoms, an alkoxy group having 1 to 6 carbon atoms, an alkanoyl group having 2 to 6 carbon atoms, an alkanoyloxy group having 2 to 6 carbon atoms, an alkyloxycarbonyl group having 2 to 6 carbon atoms, a trifluoromethyl group, or a fluorine atom.

Due to the reason that the light resistance of the compound represented by the General Formula (I) is increased, it is preferable that $A^1$, $A^2$, $A^3$, and $A^4$ in General Formula (I) each independently represent a group represented by the General Formula (B-1) or (B-2). Further, in a case where $A^1$, $A^2$, $A^3$, and $A^4$ in the General Formula (I) represent a group represented by the General Formula (B-1) or (B-2), $W^1$ and $W^2$ in the General Formula (B-1) preferably do not represent N at the same time, and $W^3$ and $W^4$ preferably do not represent N at the same time. Further, $W^5$ and $W^6$ in the General Formula (B-2) preferably do not represent N at the same time, and $W^9$ and $W^{10}$ preferably do not represent N at the same time.

$A^1$, $A^2$, $A^3$, and $A^4$ in the General Formula (I) may be a group formed by linking two or three groups represented by any of the General Formulae (B-1) to (B-7). The group formed by linking two or three groups represented by any of the General Formulae (B-1) to (B-7) may be a group formed by linking groups having the same structure may be a group formed by linking groups having structures different from each other. For example, examples of the group formed by linking two groups represented by the General Formula (B-1) include a group represented by the following General Formula (B-1-2).

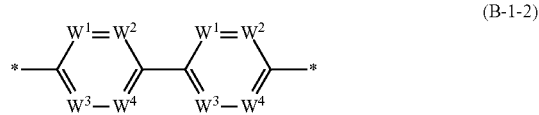
(B-1-2)

In the General Formula (B-1-2), $W^1$ to $W^4$ each independently represent $CR^1$ or N, where $R^1$ represents a hydrogen atom or the above-described substituent L. A plurality of $W^1$'s to $W^4$'s may be the same or different from each other.

Due to the reason that the compound represented by the General Formula (I) has high solubility, it is preferable that at least one of $A^1$, $A^2$, $A^3$, or $A^4$ in the General Formula (I) has the above-described substituent L.

The compound represented by the General Formula (I) is preferably a compound represented by the following General Formula (I-2) or (I-3).

In the General Formulae (I-2) and (I-3),
$T^1$ and $T^2$ each independently represent a hydrogen atom or a methyl group,
r represents an integer of 1 to 5,
t and v each independently represent 0 or 1,
u represents 1 or 2,
w represents an integer of 1 to 5,
$Q^1$ to $Q^{16}$ each independently represent a hydrogen atom or the substituent L, and
$E^1$ to $E^6$ each independently represent a hydrogen atom or the substituent L.

$T^1$ and $T^2$ preferably represent a hydrogen atom.
r preferably represents an integer of 1 to 4, more preferably represents an integer of 2 to 4, still more preferably represents 2 or 3, and particularly preferably represents 2.
t preferably represents 0.
u preferably represents 1.
v preferably represents 1.
w preferably represents an integer of 1 to 4, more preferably represents an integer of 2 to 4, still more preferably represents 2 or 3, and particularly preferably represents 2.

$Q^1$ to $Q^{16}$ and $E^1$ to $E^6$ each independently represent a hydrogen atom or the above-described substituent L, and the preferred range of the substituent L is as described above.

It is preferable that at least one of $Q^5$ to $Q^{12}$ in General Formula (I-2) represents a substituent L, and more preferably one or two of $Q^5$ to $Q^{12}$ represent a substituent L.

It is preferable that at least one of $E^1$ to $E^6$ or $Q^9$ to $Q^{12}$ in General Formula (I-3) represents the substituent L, and it is more preferable that one or two of $E^1$ to $E^6$ and $Q^9$ to $Q^{12}$ represent the substituent L.

Specific examples of the compound represented by General Formula (I) are shown below, which are not limited thereto. In the following structural formulae, Me represents a methyl group, Et represents an ethyl group, and t-Bu represents a tert-butyl group.

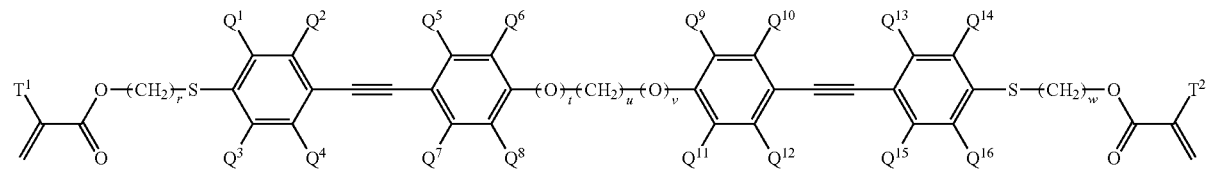
(I-2)

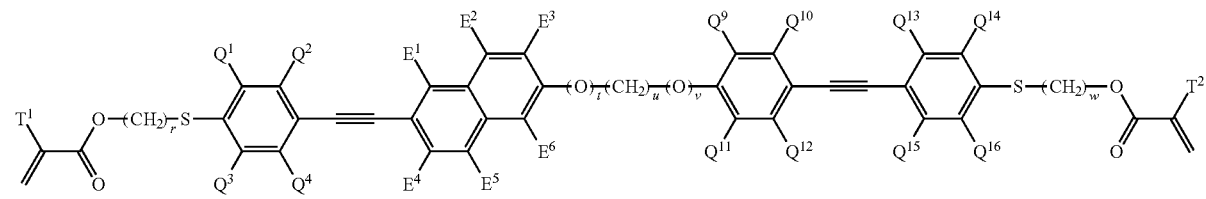
(I-3)

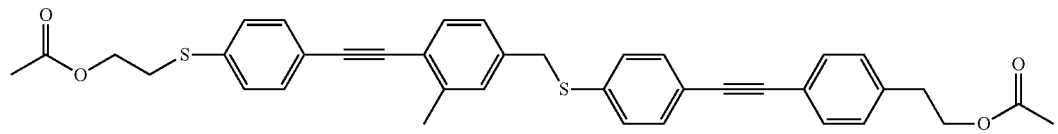
A-1
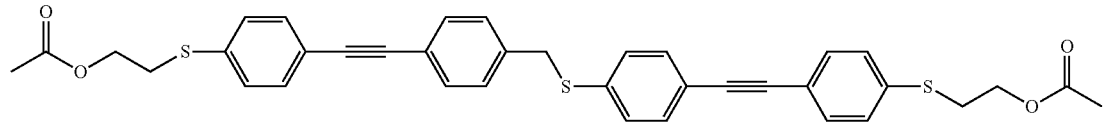
A-2
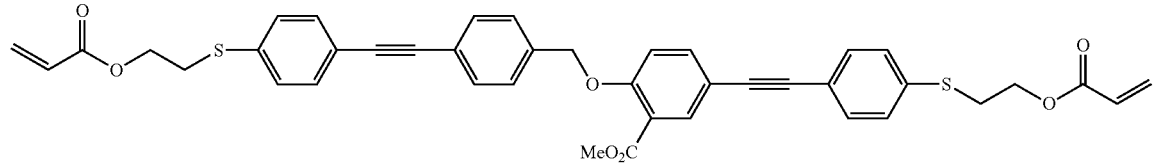
A-3
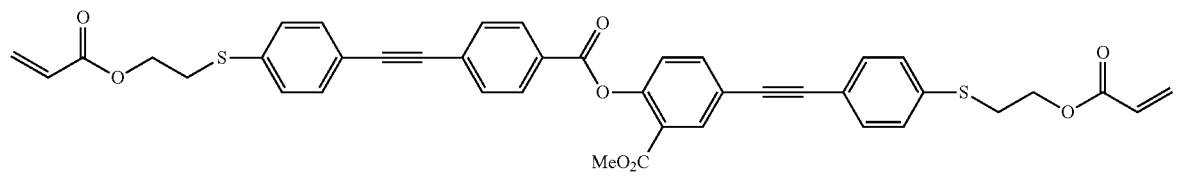
A-4
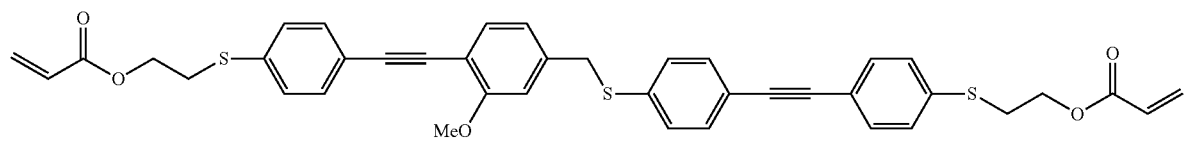
A-5
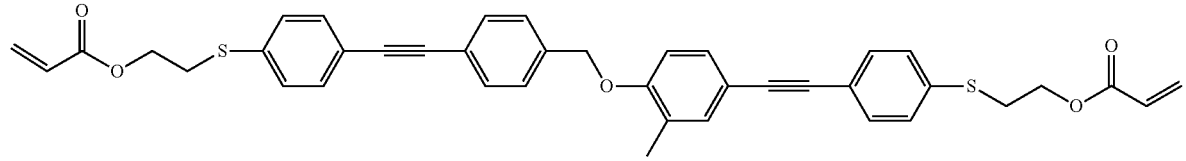
A-6
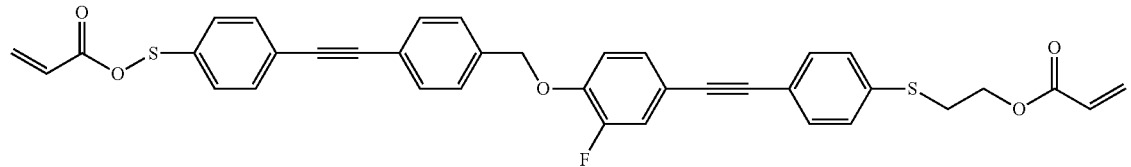
A-7
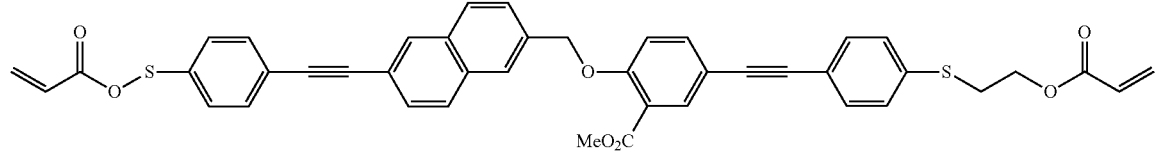
A-8
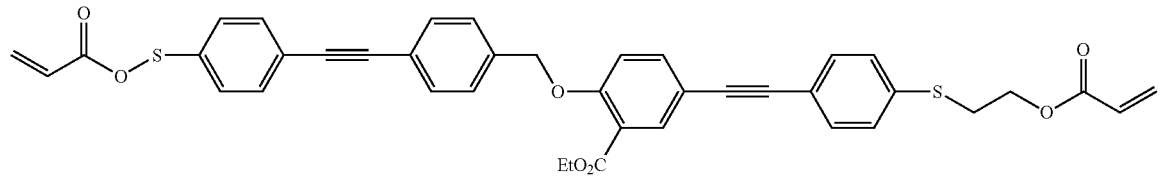
A-9

-continued
A-10
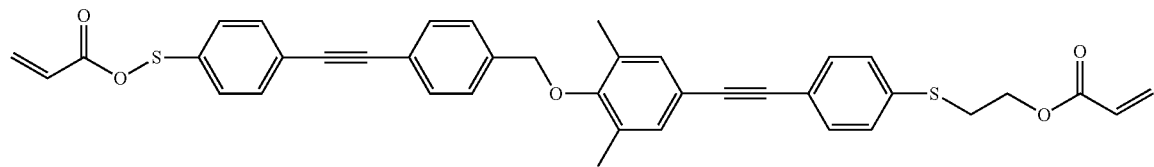
A-11
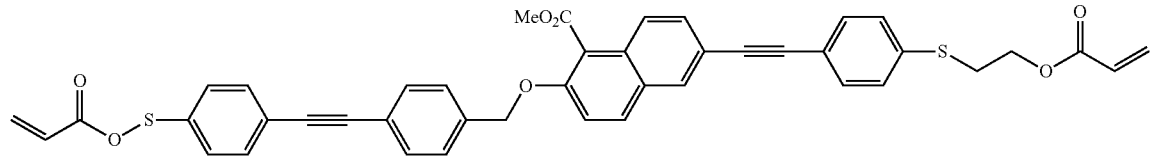
A-12
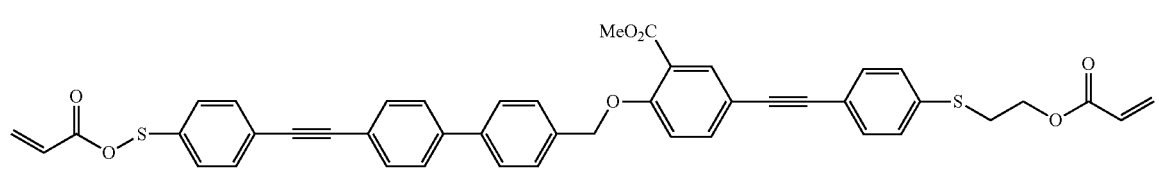
A-13
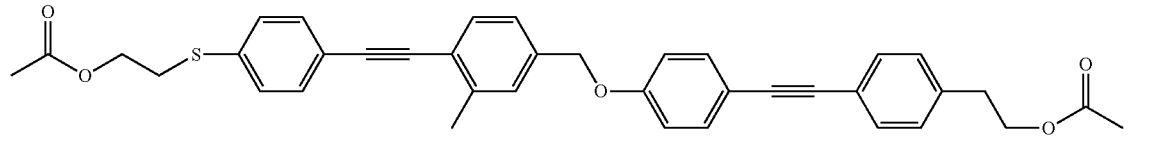
A-14
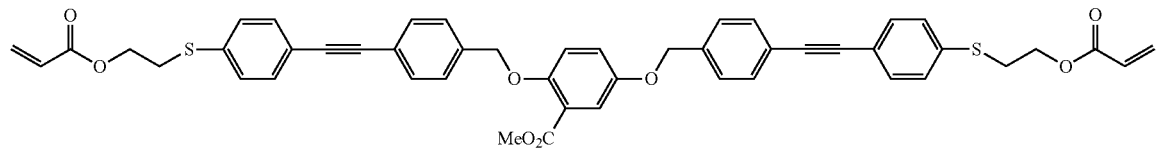
A-15
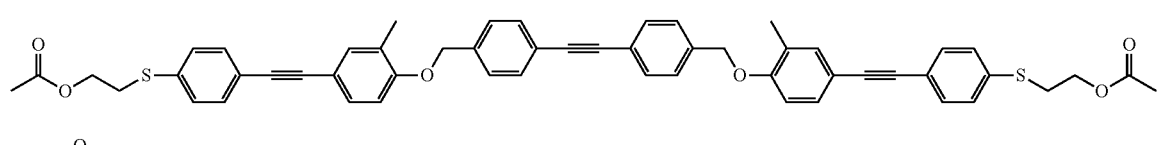
A-16
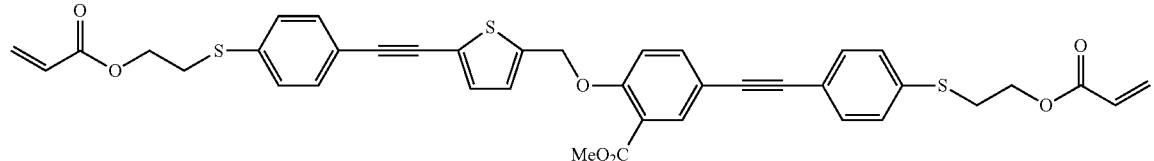
A-17
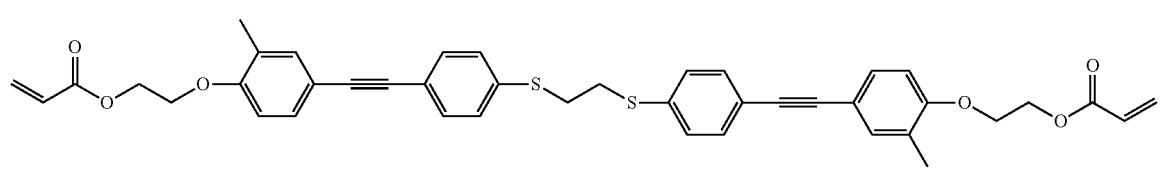
A-18
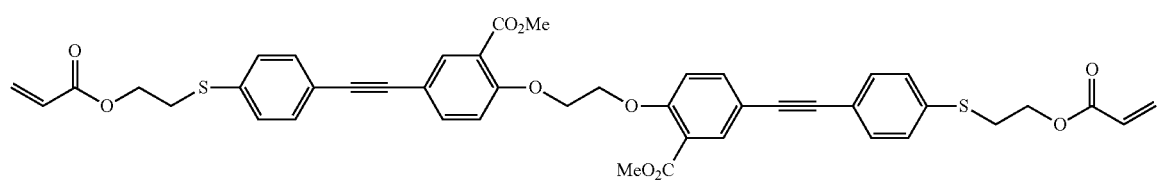

-continued
A-19
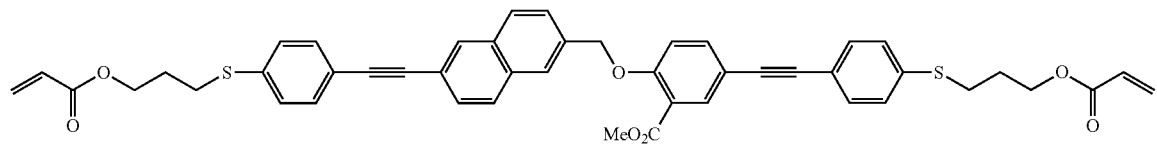
A-20
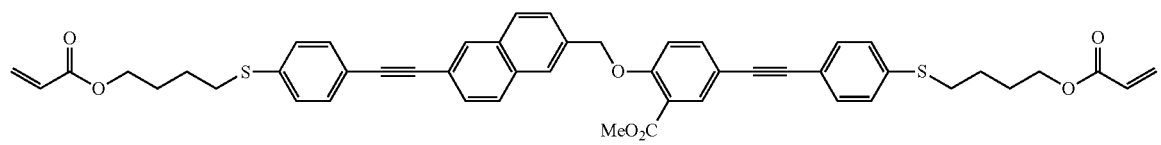
A-21
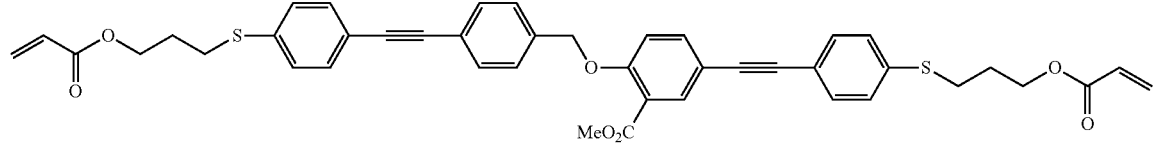
A-22
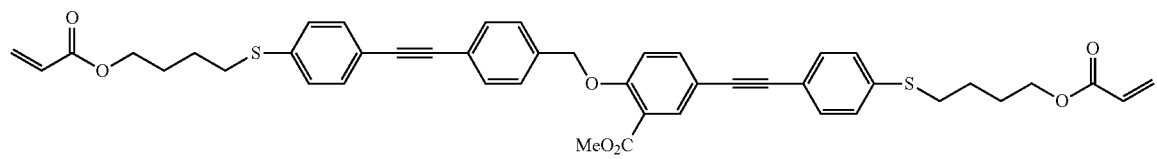
A-23
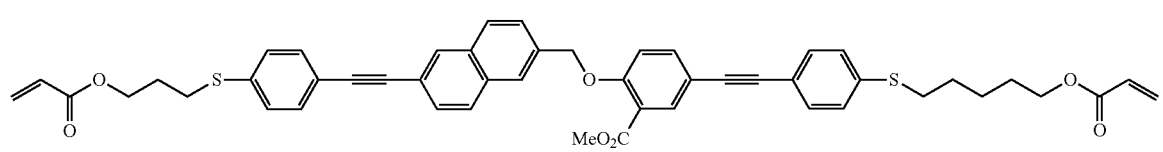
A-24
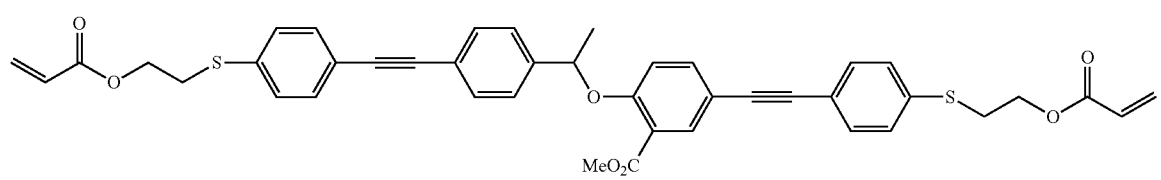
A-25
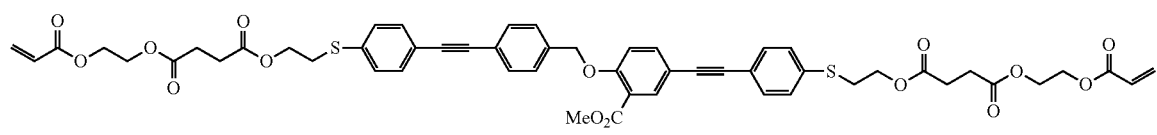
A-26
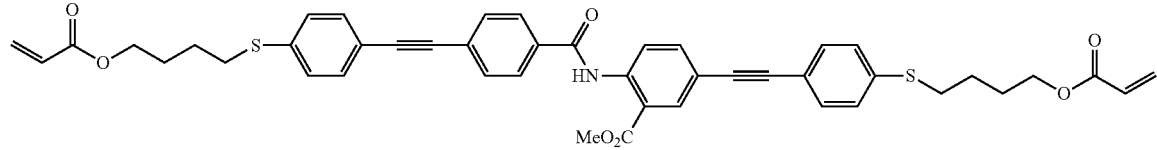
A-27
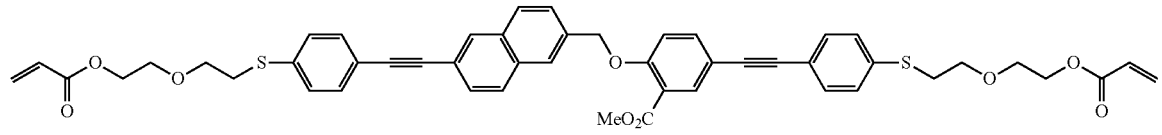

-continued
A-28
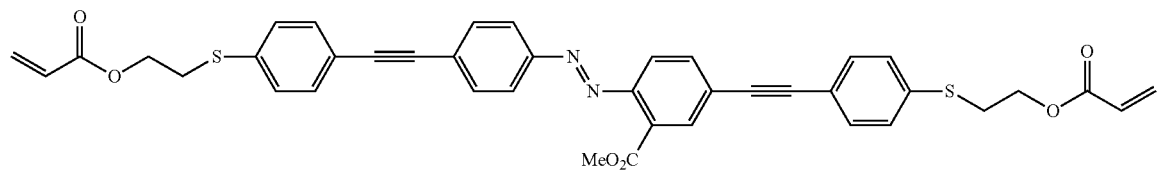
A-29
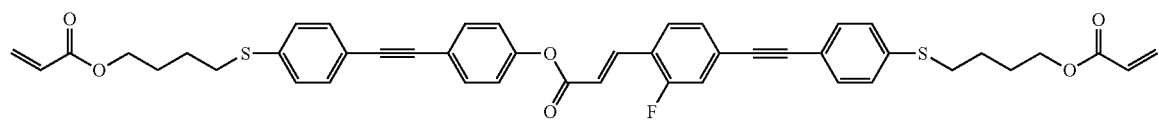
A-30
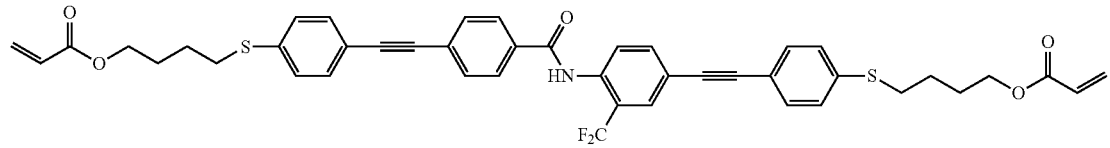
A-31
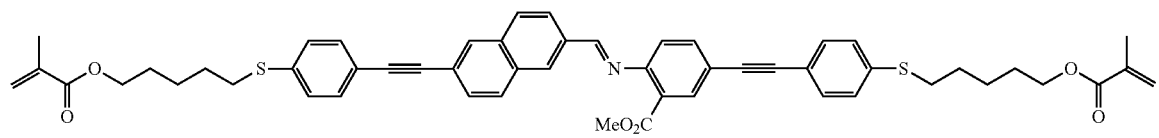
A-32
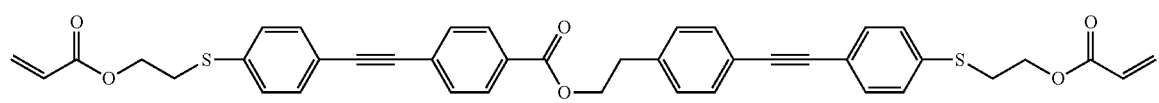
A-33
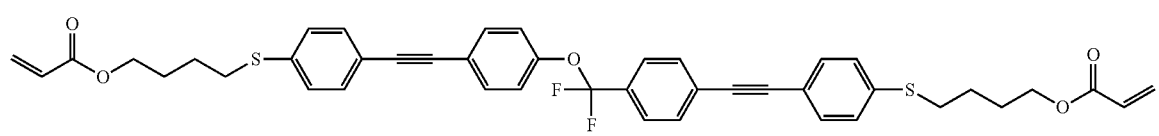
A-34
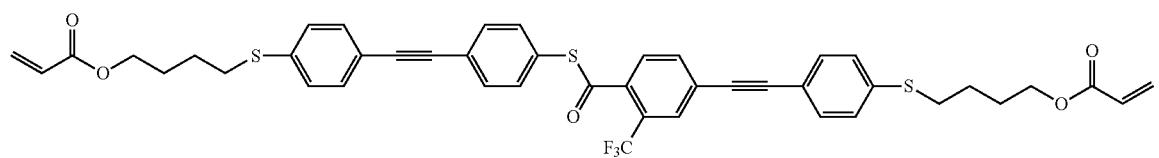
A-35
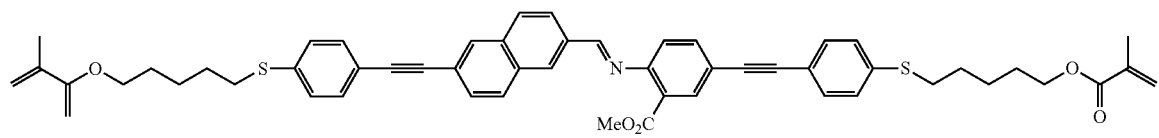
A-36
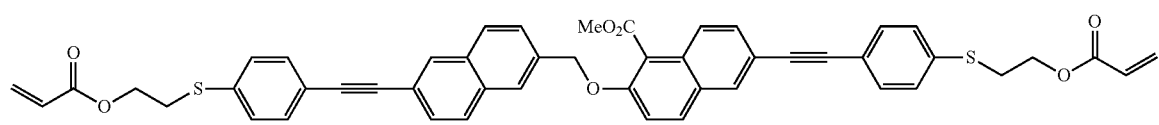

-continued
A-37
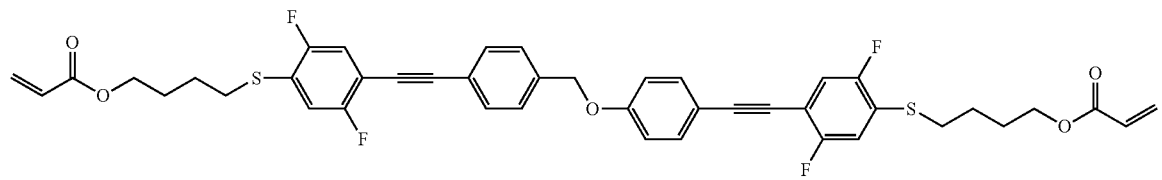
A-38
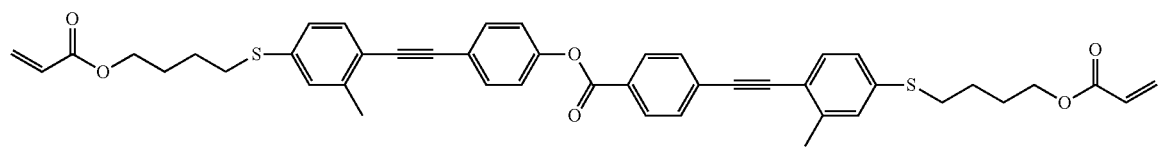
A-39
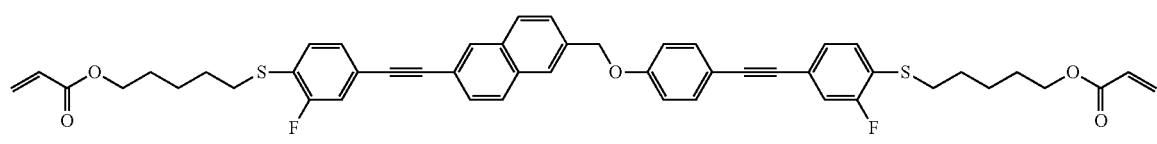
A-40
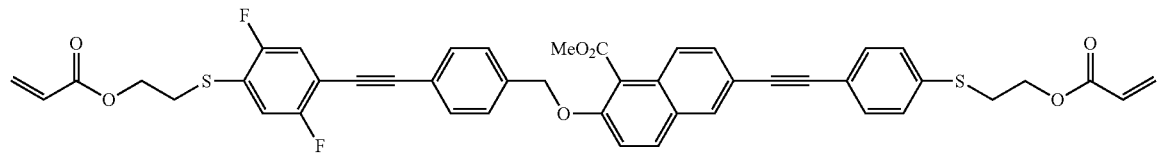
A-41
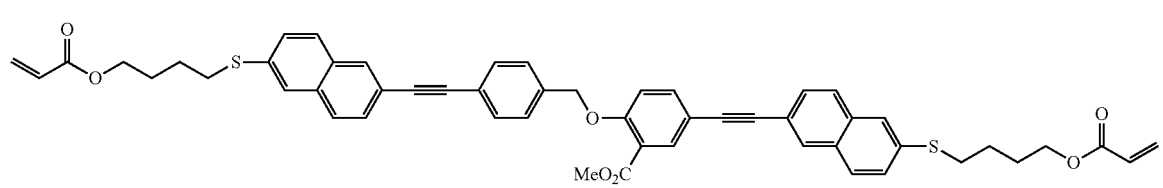
A-42
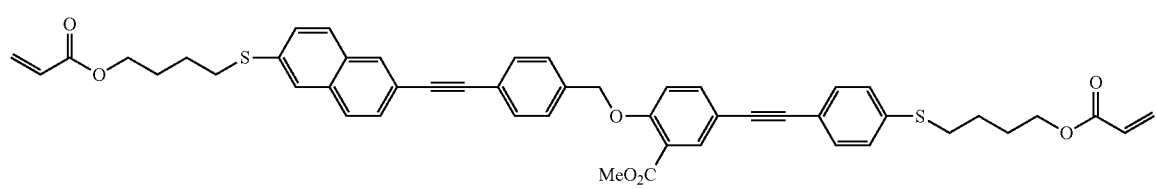
A-43
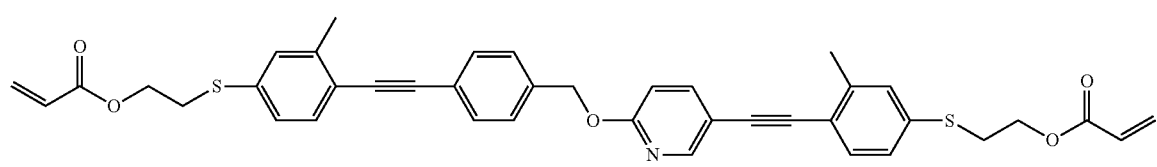
A-44
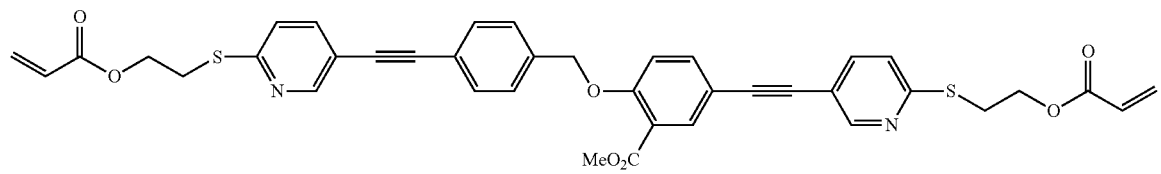

-continued
A-45
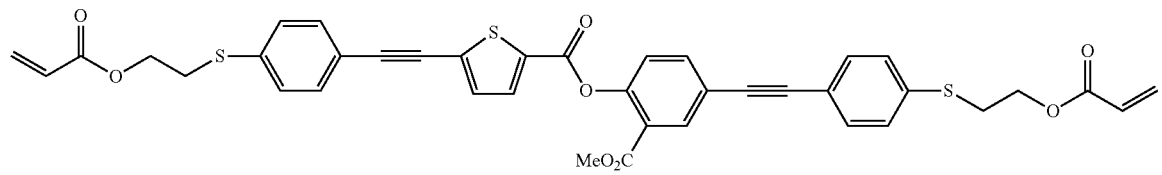
A-46
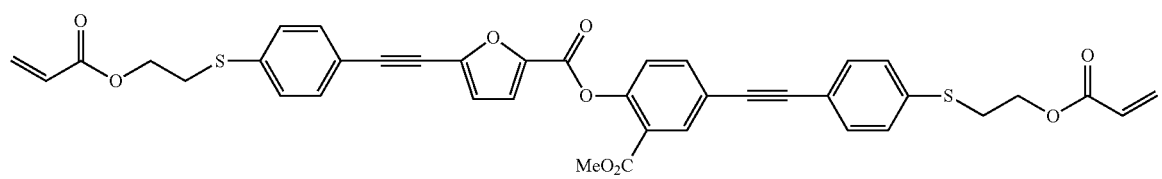
A-47
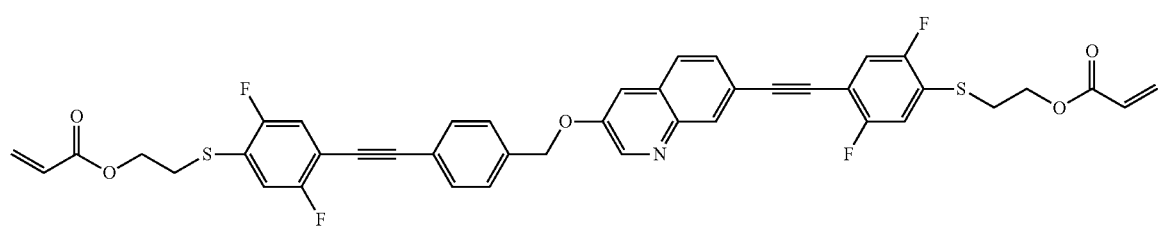
A-48
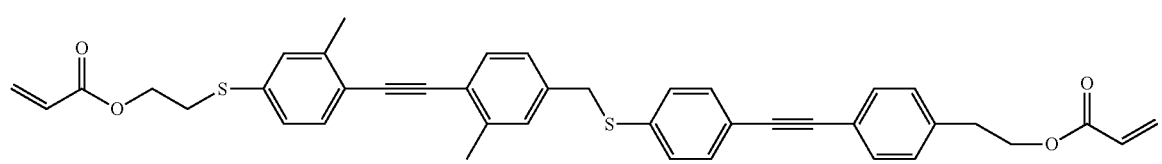
A-49
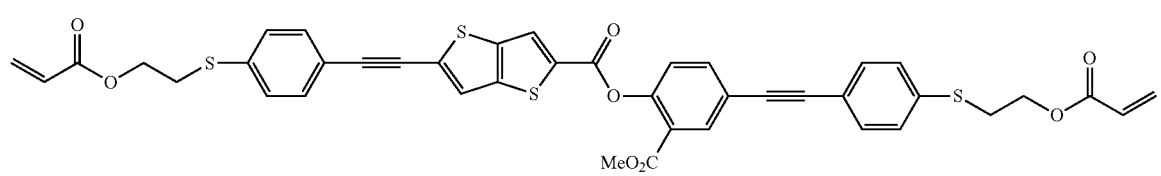
A-50
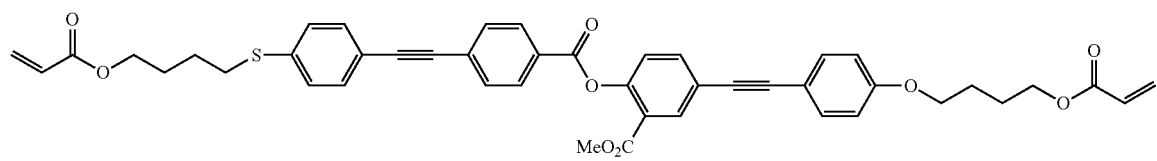
A-51
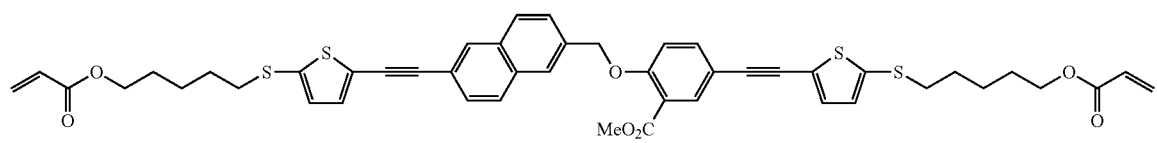
A-52
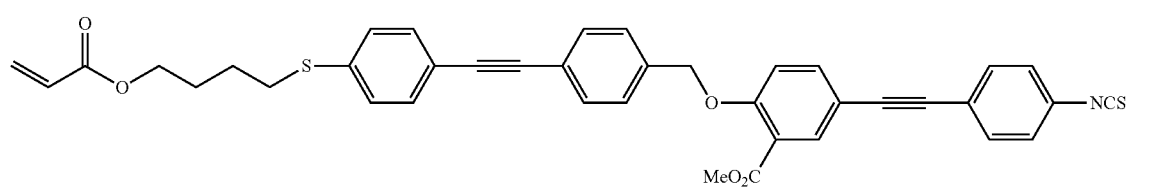

-continued
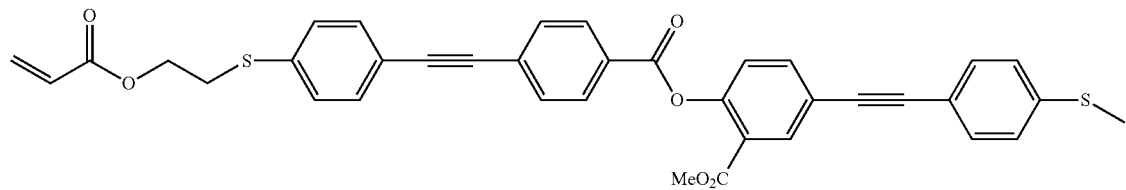
A-53
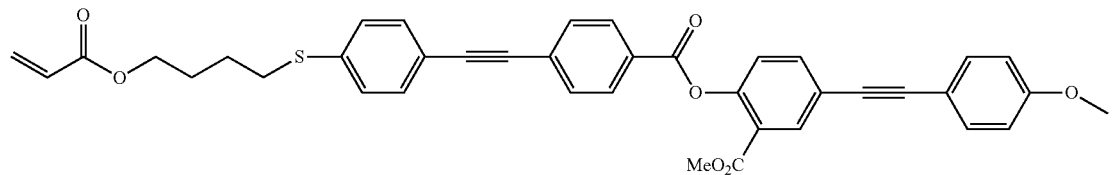
A-54
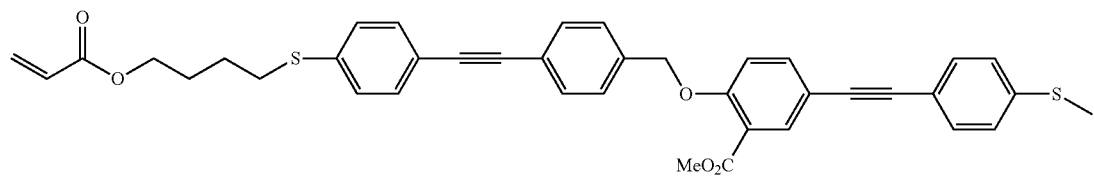
A-55
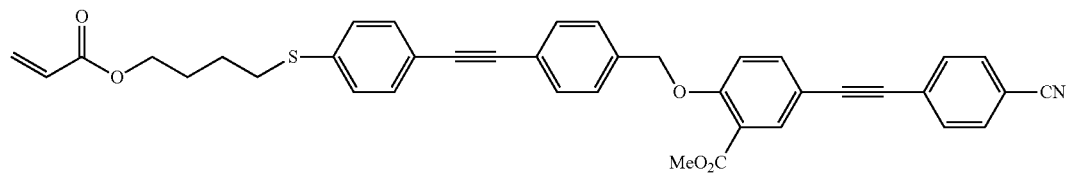
A-56
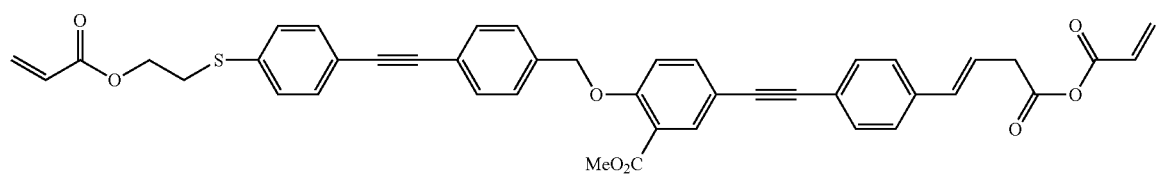
A-57
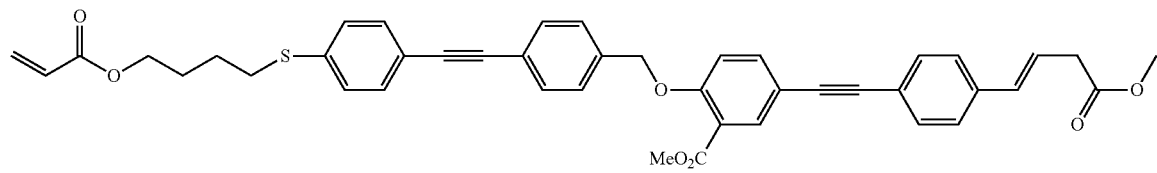
A-58
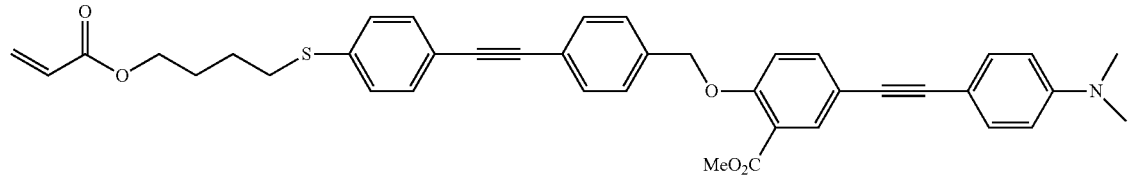
A-59
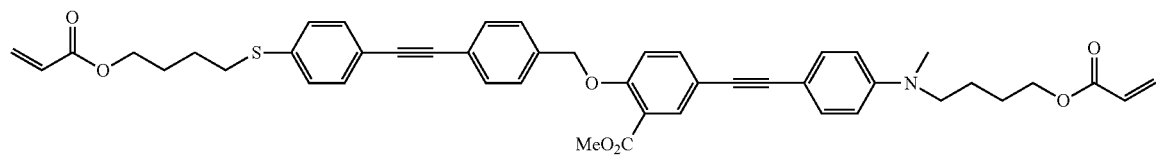
A-60

A-61
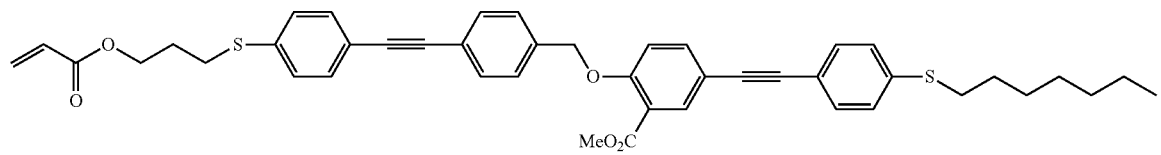
A-62
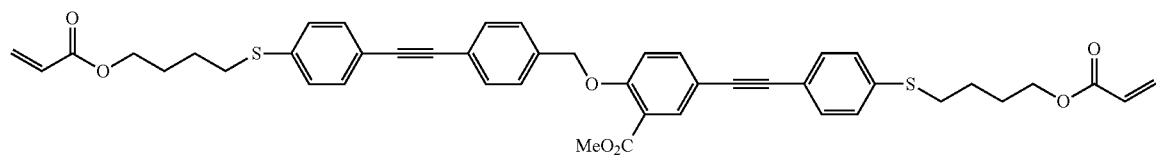
A-63
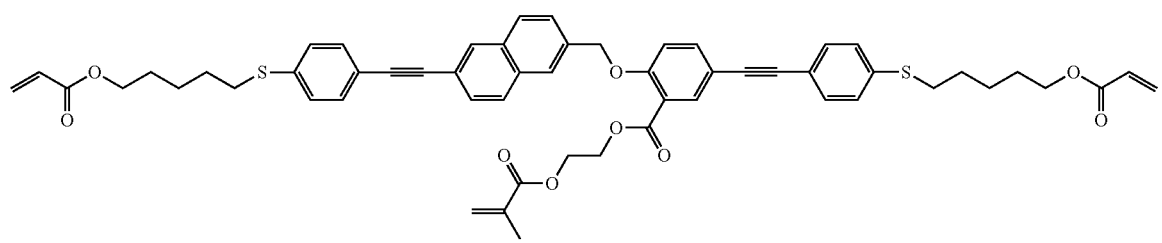
A-64
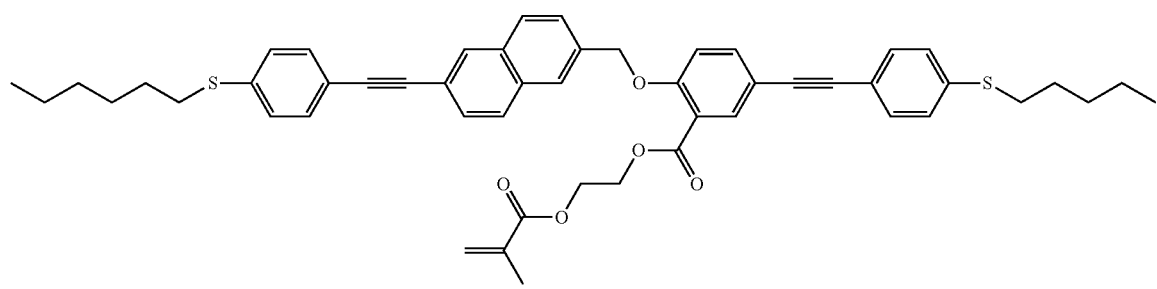
A-65
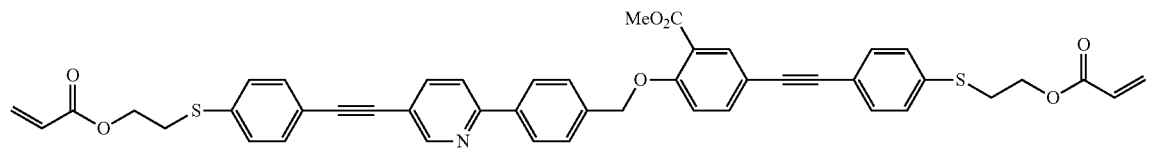
A-66
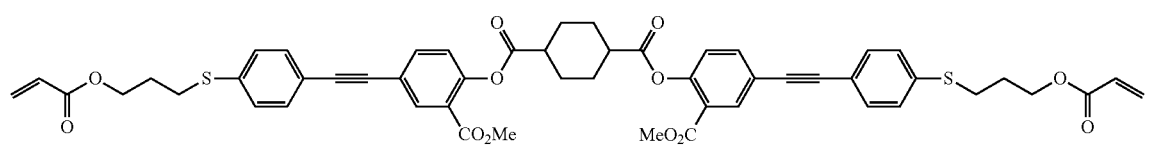
A-67
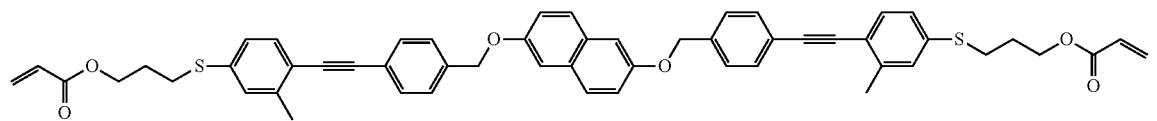
A-68
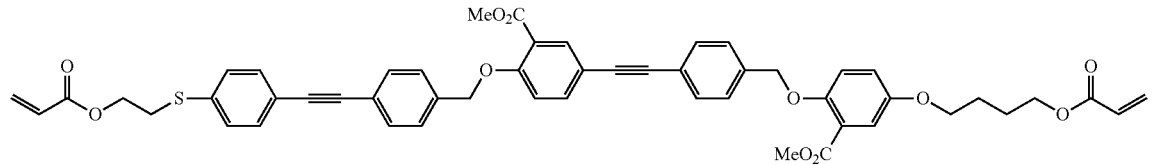

-continued
A-69
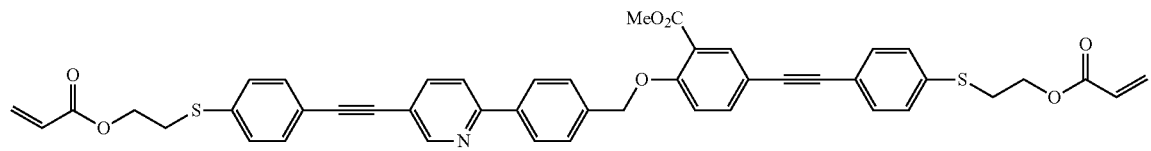
A-70
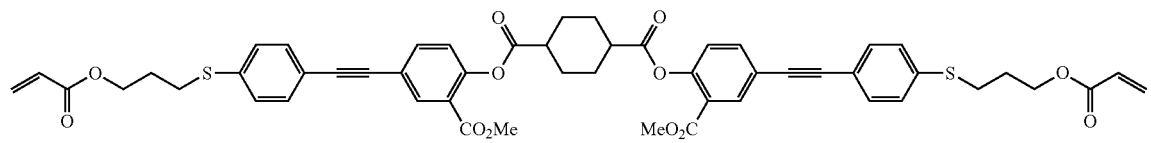
A-71
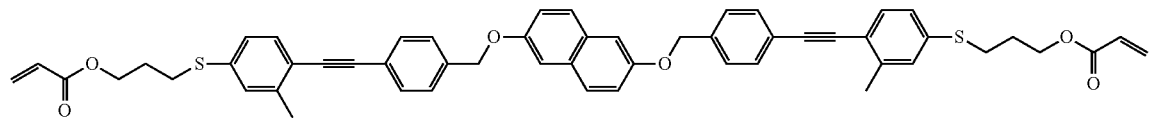
A-72
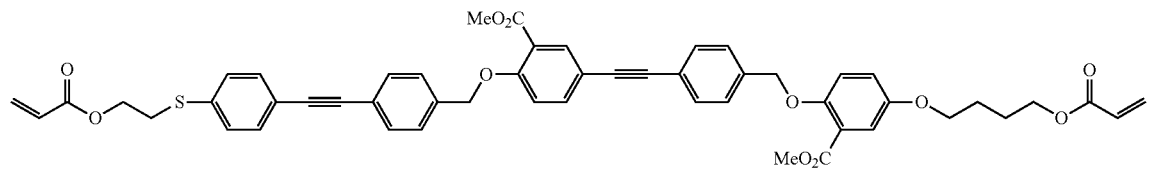
A-73
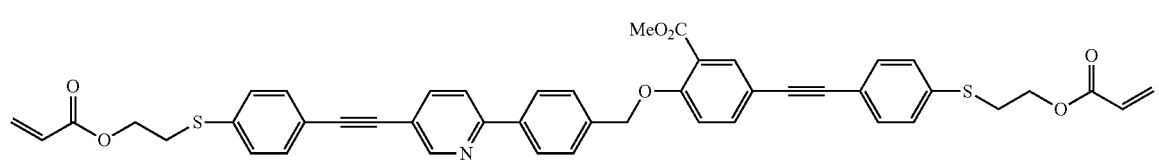
A-74
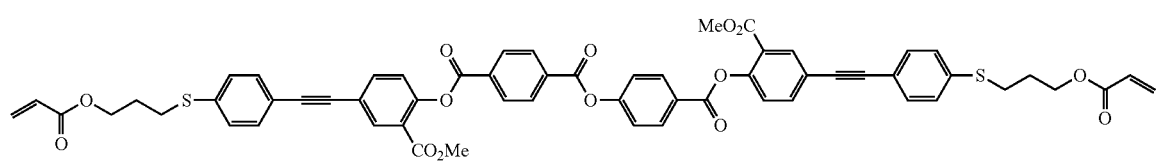
A-75
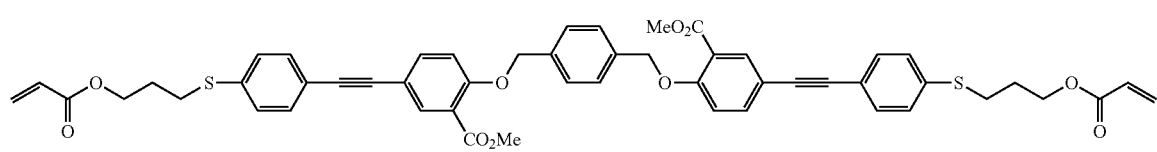
A-76
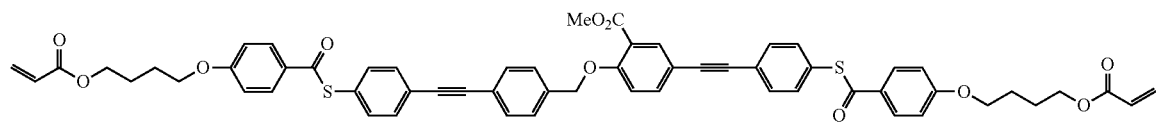
A-77
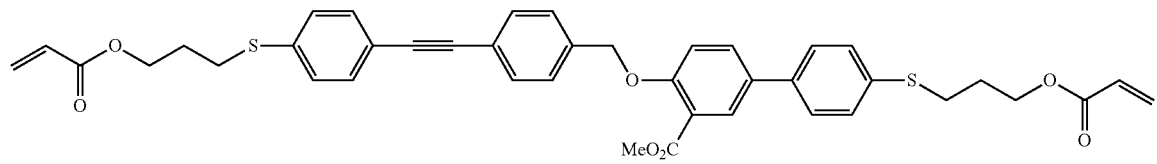

-continued
A-78
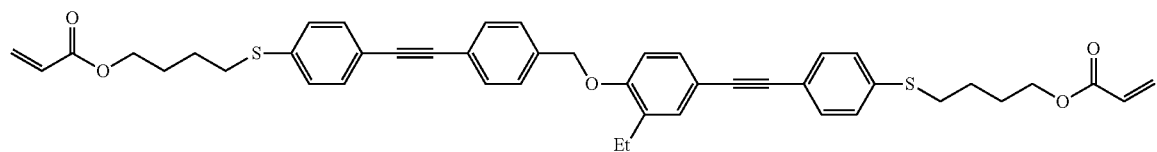
A-79
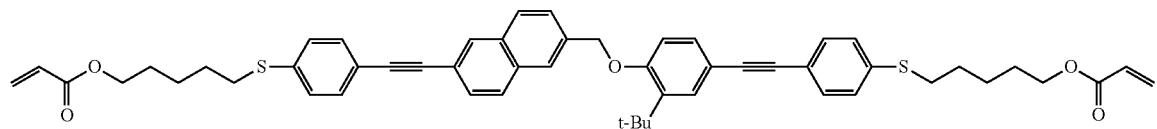
A-80
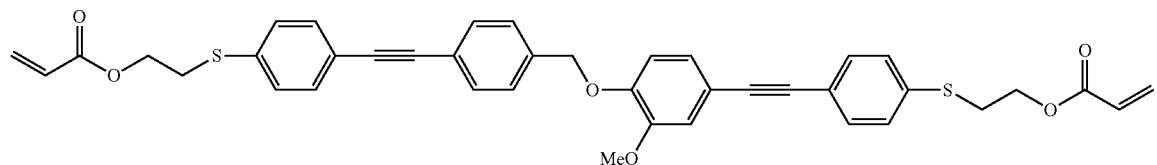
A-81
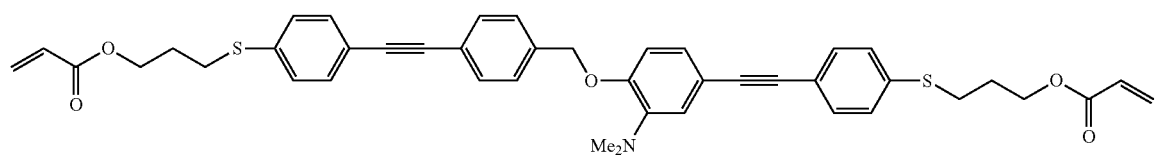
A-82
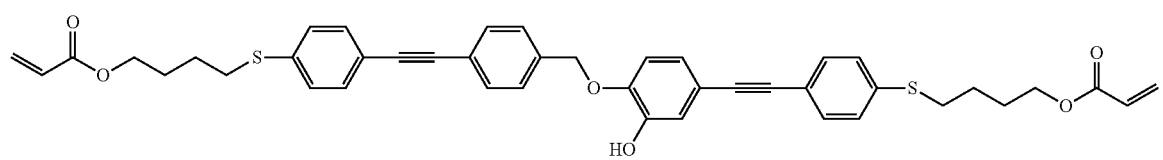
A-83
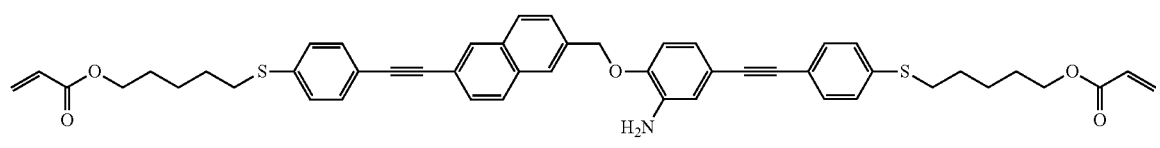
A-84
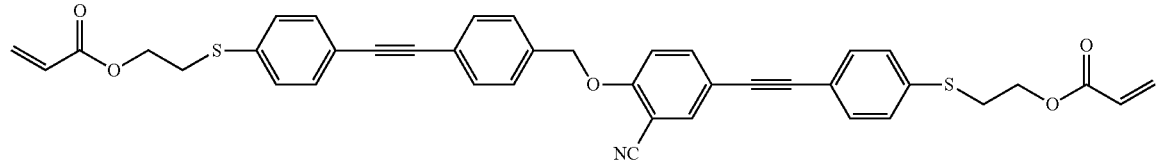
A-85
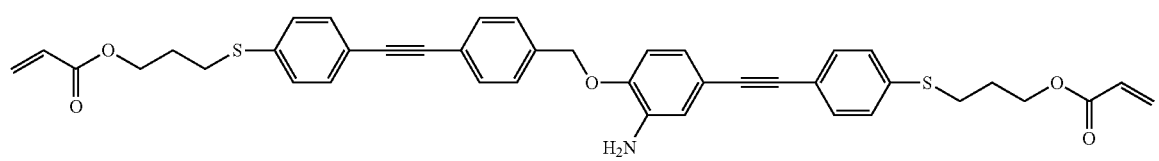
A-86
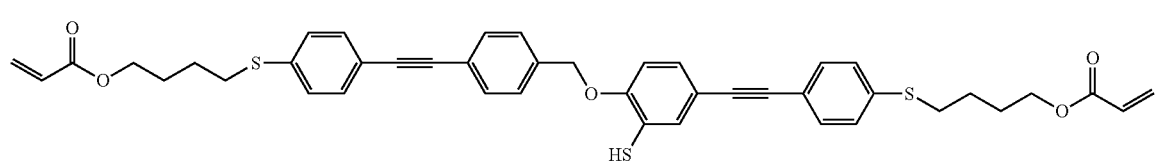

-continued
A-87
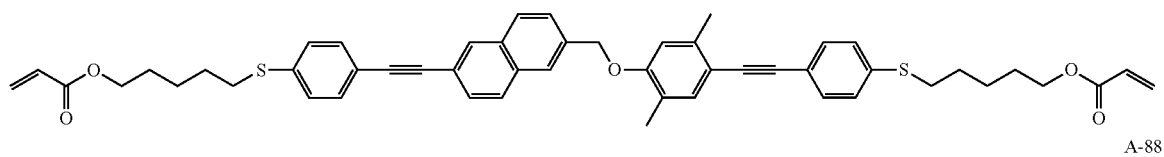
A-88
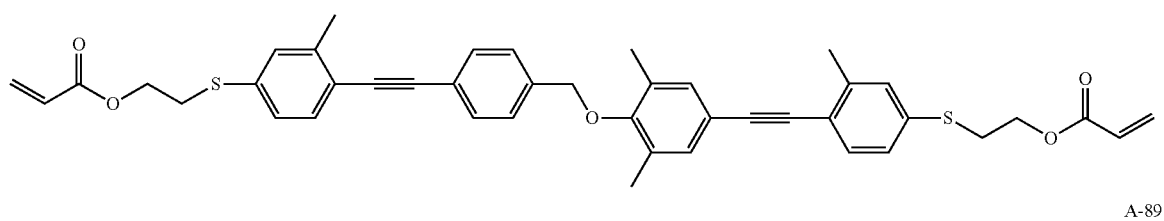
A-89
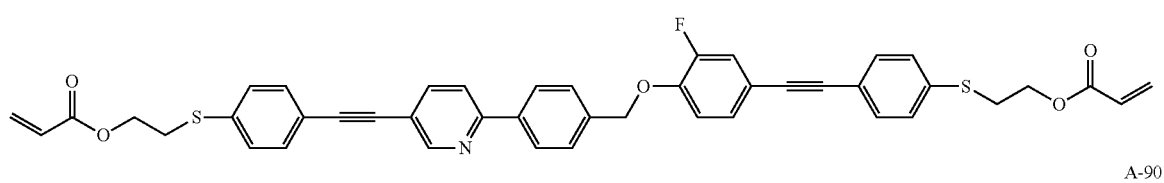
A-90
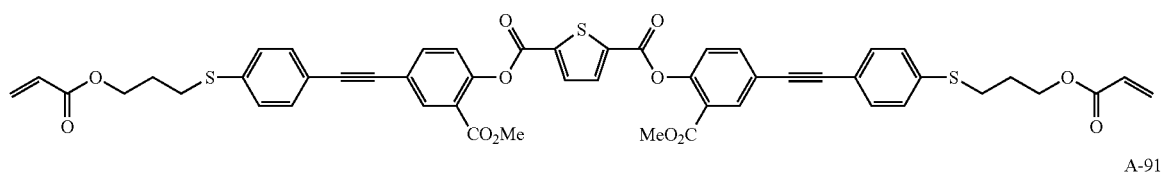
A-91
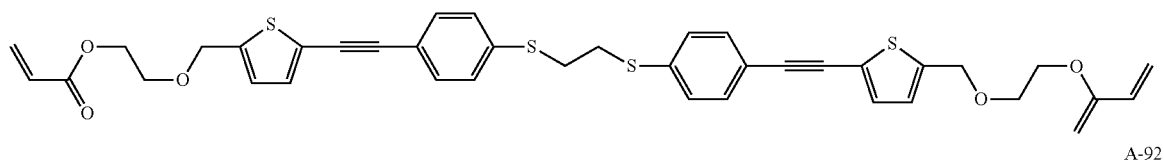
A-92
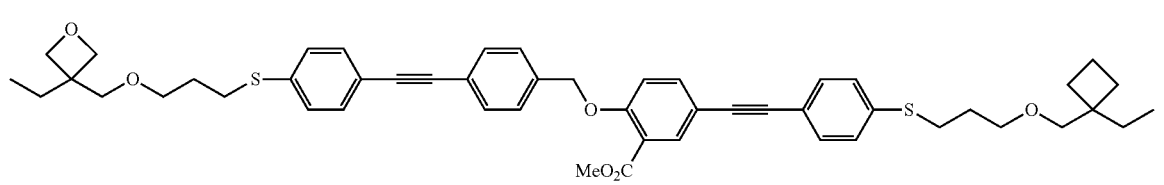
A-93
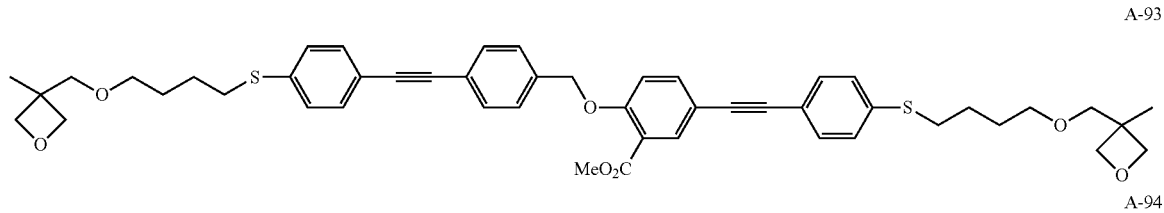
A-94
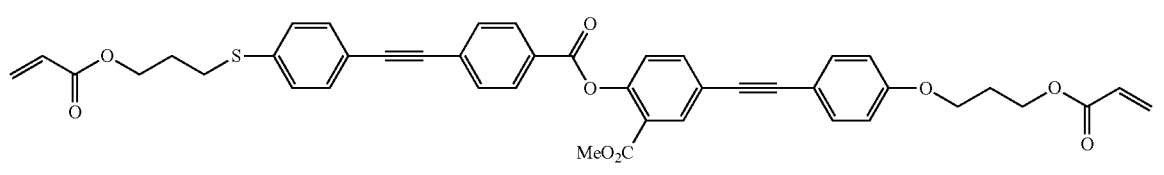
A-95
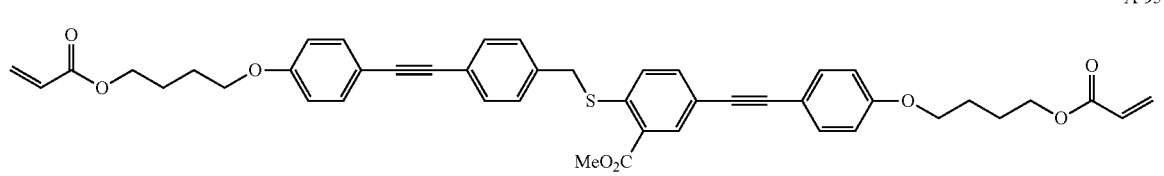

A-96

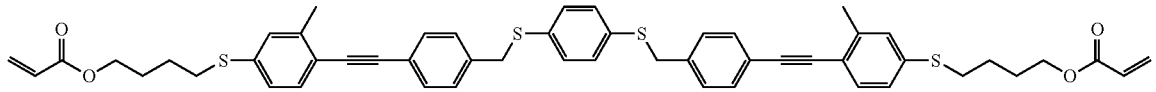

The compound represented by General Formula (I) can be synthesized by referring to or combining known methods. Specific synthesis examples of the compound represented by General Formula (I) will be described in Examples described later.

The compound represented by General Formula (I) may have or may not have liquid crystallinity; however, it preferably has liquid crystallinity.

In a case where the compound represented by General Formula (I) has liquid crystallinity, it is easy to align the compound represented by General Formula (I) and it is possible to easily produce a desired alignment pattern, which is preferable, in a case where an optically anisotropic layer is produced from a composition containing the compound represented by General Formula (I).

However, for example, in a case of being mixed with another compound having liquid crystallinity, the compound represented by General Formula (I) can be used to form a liquid crystal composition even in a case where the compound itself does not have liquid crystallinity, whereby a desired alignment pattern can be produced.

That the compound has liquid crystallinity means that the compound has properties of exhibiting a mesophase between a crystal phase (a low temperature side) and an isotropic phase (a high temperature side) in a case where the temperature is changed. As a specific observation method, optical anisotropy and fluidity derived from the liquid crystal phase can be checked by carrying out an observation under a polarization microscope while heating or lowering the temperature of the compound with a hot stage or the like.

An optical element according to the embodiment of the present invention, which will be described later, is preferably produced by dissolving a composition containing the compound represented by General Formula (I) in a solvent and applying the dissolved composition. The precipitation concentration of the compound represented by General Formula (I) at 25° C. in a solvent is preferably 10% by mass or more.

Composition containing compound represented by General Formula (I)

A composition containing the compound represented by General Formula (I) (hereinafter, also referred to as a "composition according to the embodiment of the present invention") will be described.

The content of the compound represented by General Formula (I) in the composition according to the embodiment of the present invention is not particularly limited; however, it is preferably 5% to 100% by mass, more preferably 20% to 99% by mass, still more preferably 30% to 99% by mass, and particularly preferably 40% to 99% by mass, with respect to the total mass of the solid content in the composition.

The solid content means components (non-volatile contents) other than the solvent in the composition. In a case of components other than the solvent, the components are regarded as the solid content even in a case where they are components having properties of a liquid.

In the composition, one kind of the compound represented by General Formula (I) may be used alone, or two or more kinds thereof may be used. In a case where two or more kinds are used, the total content thereof is preferably within the above-described range.

The composition according to the embodiment of the present invention may have or may not have liquid crystallinity; however, it preferably has liquid crystallinity.

In a case where the composition according to the embodiment of the present invention has liquid crystallinity, it is easy to align the compound in the composition, and it is possible to easily produce a desired alignment pattern, which is preferable, in a case where an optically anisotropic layer is produced from the composition.

That the composition has liquid crystallinity means that the composition has properties of exhibiting a mesophase between a crystal phase (a low temperature side) and an isotropic phase (a high temperature side) in a case where the temperature is changed. As a specific observation method, optical anisotropy and fluidity derived from the liquid crystal phase can be checked by carrying out an observation under a polarization microscope while heating or lowering the temperature of the composition with a hot stage or the like.

The composition according to the embodiment of the present invention is preferably a composition for forming an optically anisotropic layer.

The composition according to the embodiment of the present invention may contain other components in addition to the compound represented by General Formula (I).

Hereinafter, the other components will be described.
Another Liquid Crystal Compound The composition according to the embodiment of the present invention may contain a liquid crystal compound (also referred to as "another liquid crystal compound") that is not a compound represented by General Formula (I).

The other liquid crystal compound may be a rod-shaped liquid crystal compound or a disc-shaped liquid crystal compound, but a rod-shaped liquid crystal compound is preferable. In addition, the other liquid crystal compound is preferably a liquid crystal compound having a polymerizable group (another polymerizable liquid crystal compound).

Examples of the rod-shaped liquid crystal compound which is the other liquid crystal compound include a rod-shaped nematic liquid crystal compound. Preferable examples of the rod-shaped nematic liquid crystal compounds include azomethines, azoxys, cyanobiphenyls, cyanophenyl esters, benzoic acid esters, cyclohexanecarboxylic acid phenyl esters, cyanophenylcyclohexanes, cyano-substituted phenylpyrimidines, alkoxy-substituted phenylpyrimidines, phenyldioxanes, tolans, and alkenylcyclohexylbenzonitriles. As the other liquid crystal compound, not only a liquid crystal compound having a low molecular weight but also a polymer liquid crystal compound can be used.

The liquid crystal compound having a polymerizable group can be obtained by introducing the polymerizable group into the liquid crystal compound. Examples of the polymerizable group include the polymerizable group exemplified as $P^1$ and $P^2$ of General Formula (I).

The liquid crystal compound having polymerizable groups preferably has 1 to 6 polymerizable groups and more preferably 1 to 3 polymerizable groups.

In the other liquid crystal compound, the refractive index anisotropy Δn is preferably high. Specifically, it is preferably 0.15 or more, more preferably 0.18 or more, and still more preferably 0.22 or more. The upper limit thereof is not particularly limited; however, it is 0.60 or less in many cases.

In addition, in a case where the compound represented by General Formula (I) is mixed with the other liquid crystal compounds and used, the crystallization temperature as a whole can be significantly lowered.

Examples of other liquid crystal compounds include compounds disclosed in Makromol. Chem., Vol. 190, page 2255 (1989), Advanced Materials, Vol. 5, page 107 (1993), U.S. Pat. Nos. 4,683,327A, 4,983,479A, 5,622,648A, 5,770,107A, WO95/22586A, WO95/24455A, WO97/00600A, WO98/23580A, WO98/52905A, JP1989-272551A (JP-H1-272551A), JP1994-16616A (JP-H6-16616A), JP1995-110469A (JP-H7-110469A), JP1999-80081A (JP-H11-80081A), JP2001-328973A.

In a case where the composition according to the embodiment of the present invention contains another liquid crystal compound, the content of the other liquid crystal compound in the composition is not particularly limited; however, it is preferably 95% by mass or less, more preferably 1% to 80% by mass, still more preferably 1% to 70% by mass, and particularly preferably 1% to 60% by mass, with respect to the total mass of the solid content in the composition.

In the composition according to the embodiment of the present invention, one kind of another liquid crystal compound may be used alone, or two or more kinds thereof may be used. In a case where two or more kinds are used, the total content thereof is preferably within the above-described range.

Polymerization Initiator

The composition according to the embodiment of the present invention may contain a polymerization initiator.

The polymerization initiator is preferably a photopolymerization initiator which is capable of initiating a polymerization reaction by ultraviolet irradiation. Examples of the photopolymerization initiator include an α-carbonyl compound, an acyloin ether, an α-hydrocarbon-substituted aromatic acyloin compound, a polynuclear quinone compound, a phenazine compound, and an oxadiazole compound. In addition, a compound having an oxime ester structure is also preferable.

In a case where the composition according to the embodiment of the present invention contains a polymerization initiator, the content of the polymerization initiator in the composition is not particularly limited; however, it is preferably 0.1% to 20% by mass, and it is more preferably 1% to 8% by mass, with respect to the total mass of the compound represented by General Formula (I) (with respect to the total mass of the compound represented by General Formula (I) and another liquid crystal compound in a case where the composition contains the other liquid crystal compound).

In the composition according to the embodiment of the present invention, one kind of polymerization initiator may be used alone, or two or more kinds thereof may be used. In a case where two or more kinds are used, the total content thereof is preferably within the above-described range.

Surfactant

The composition according to the embodiment of the present invention may contain a surfactant that contributes to the formation of a stable or rapid liquid crystal phase (for example, a nematic phase, a cholesteric phase).

Examples of the surfactant include a fluorine-containing (meth)acrylate-based polymer, compounds represented by General Formulae (X1) to (X3) disclosed in WO2011/162291A, compounds represented by General Formula (I) disclosed in paragraphs 0082 to 0090 of JP2014-119605A, and compounds disclosed in paragraphs 0020 to 0031 of JP2013-47204A.

Examples of the fluorine-containing (meth)acrylate-based polymer that can be used as a surfactant also include polymers disclosed in paragraphs 0018 to 0043 of JP2007-272185A.

In a case where the composition according to the embodiment of the present invention contains a surfactant, the content of the surfactant is not particularly limited; however, it is preferably 0.001% to 10% by mass and more preferably 0.05% to 3% by mass with respect to the total mass of the compound represented by General Formula (I) (with respect to the total mass of the compound represented by General Formula (I) and another liquid crystal compound in a case where the composition contains the other liquid crystal compound).

In the composition according to the embodiment of the present invention, one kind of surfactant may be used alone, or two or more kinds thereof may be used. In a case where two or more kinds are used, the total content thereof is preferably within the above-described range.

Chiral Agent

The composition according to the embodiment of the present invention may contain a chiral agent. In a case where the composition according to the embodiment of the present invention contains a chiral agent, a cholesteric phase can be formed.

The kind of the chiral agent is not particularly limited. The chiral agent may be liquid crystalline or non-liquid crystalline. The chiral agent generally contains an asymmetric carbon atom. However, an axial asymmetric compound or a planar asymmetric compound, which does not contain any asymmetric carbon atom, can also be used as the chiral agent. Examples of the axial asymmetric compound or the planar asymmetric compound include binaphthyl, helicene, paracyclophane, and a derivative thereof. The chiral agent may have a polymerizable group.

In a case where the composition according to the embodiment of the present invention contains a chiral agent, the content of the chiral agent in the composition is not particularly limited; however, it is preferably 0.1% to 15% by mass and more preferably 1.0% to 10% by mass with respect to the total mass of the compound represented by General Formula (I) (with respect to the total mass of the compound represented by General Formula (I) and another liquid crystal compound in a case where the composition contains the other liquid crystal compound).

In the composition according to the embodiment of the present invention, one kind of chiral agent may be used alone, or two or more kinds thereof may be used. In a case where two or more kinds are used, the total content thereof is preferably within the above-described range.

Solvent

The composition of the embodiment of the present invention may contain a solvent. The solvent is preferably a solvent capable of dissolving each component of the composition according to the embodiment of the present invention, and examples thereof include chloroform and methyl ethyl ketone. In a case where the composition according to the embodiment of the present invention contains the solvent, the content of the solvent in the composition is such an amount that the concentration of solid contents of the composition is preferably 0.5% to 20% by mass and more preferably 1% to 10% by mass.

In the composition according to the embodiment of the present invention, one kind of solvent may be used alone, or two or more kinds thereof may be used. In a case where two or more kinds are used, the total content thereof is preferably within the above-described range.

In addition to the above, the composition according to the embodiment of the present invention may also contain other components such as an antioxidant, an ultraviolet absorber, a sensitizer, a stabilizer, a plasticizer, a chain transfer agent, a polymerization inhibitor, an anti-foaming agent, a leveling agent, a thickener, a flame retardant, a surfactant, a dispersing agent, and a coloring material such as a dye or a pigment.

In addition, it is also preferable that the optically anisotropic layer can be made to be responsive to substantially a wide range of wavelengths of incident light by imparting a twisting component to the composition according to the embodiment of the present invention or by laminating different retardation layers. For example, JP2014-089476A or the like discloses a method of realizing Δ/2 plate having a wide-range pattern by laminating two liquid crystal layers having different twisted directions in an optically anisotropic layer, which can be preferably used in the optical element according to the embodiment of the present disclosure.

Cured Substance and Optically Anisotropic Body

A cured substance that is obtained by curing the composition according to the embodiment of the present invention, and an optically anisotropic body will be described.

A method of curing (polymerizing and curing) the composition according to the embodiment of the present invention is not particularly limited, and a known method can be adopted. Examples thereof include an aspect having a step X of bringing a predetermined substrate into contact with a composition to form a composition layer on the substrate and a step Y of subjecting the composition layer to a heat treatment so that the compound represented by General Formula (I) is aligned and then subjecting it to a curing treatment. According to this aspect, the compound represented by General Formula (I) can be immobilized in an aligned state, whereby an optically anisotropic body (for example, an optically anisotropic layer) can be formed.

Hereinafter, procedures for the step X and the step Y will be described in detail.

The step X is a step of bringing a predetermined substrate into contact with a composition to form a composition layer on the substrate. The kind of the substrate to be used is not particularly limited, and examples thereof include known substrates (for example, a resin substrate, a glass substrate, a ceramic substrate, a semiconductor substrate, and a metal substrate).

The method of bringing a substrate into contact with a composition is not particularly limited, and examples thereof include a method of applying a composition onto a substrate and a method of immersing a substrate in a composition.

It is noted that after bringing a substrate into contact with a composition, as necessary, a drying treatment may be carried out in order to remove a solvent from the composition layer on the substrate.

The step Y is a step of subjecting the composition layer to a heat treatment so that the compound represented by General Formula (I) invention is aligned, and then subjecting it to a curing treatment.

In a case where the composition layer is subjected to a heat treatment, the compound represented by General Formula (I) is aligned and a liquid crystal phase is formed. For example, in a case where a chiral agent is contained in the composition layer, a cholesteric liquid crystalline phase is formed.

The conditions for the heat treatment are not particularly limited, and optimal conditions are selected depending on the kind of the compound represented by General Formula (I).

The method for the curing treatment is not particularly limited, and examples thereof include a photo-curing treatment and a thermal-curing treatment. Among these, a light irradiation treatment is preferable, and an ultraviolet irradiation treatment is more preferable.

For ultraviolet irradiation, a light source such as an ultraviolet lamp is used.

The cured substance that is obtained by the above treatment corresponds to a layer that is obtained by fixing a liquid crystal phase. In particular, in a case where the composition contains a chiral agent, a layer that is obtained by fixing a cholesteric liquid crystalline phase is formed.

It is noted that these layers do not need to exhibit liquid crystallinity anymore. More specifically, for example, as a state in which the cholesteric liquid crystalline phase is "fixed," the most typical and preferred aspect is a state in which the alignment of the compound represented by General Formula (I) which is in the cholesteric liquid crystalline phase is retained. More specifically, it is preferably a state in which within a temperature range of usually 0° C. to 50° C., or −30° C. to 70° C. under the more severe conditions, no fluidity is exhibited in the layer, no changes in alignment form occur due to an external field or an external force, and a fixed alignment form can be kept stably and continuously.

Optical Element

The optical element according to the embodiment of the present invention is an optical element that has an optically anisotropic layer formed from the above-described composition according to the embodiment of the present invention, where the optically anisotropic layer has an alignment pattern, and the alignment pattern is an alignment pattern in which an orientation of an optical axis, derived from a compound contained in the composition, continuously changes rotationally along at least one in-plane direction.

It is preferable that the alignment pattern is an alignment pattern in which the orientation of the optical axis, derived from the compound represented by General Formula (I), continuously changes rotationally along at least one in-plane direction, or an alignment pattern in which the orientation of the optical axis, derived from the compound represented by General Formula (I) and the other liquid crystal compound, continuously changes rotationally along at least one in-plane direction.

The optical element according to the embodiment of the present invention has an alignment pattern in which the orientation of the optical axis continuously changes rotationally along at least one in-plane direction, and thus it can diffract the light incident on the optical element. Since the compound represented by General Formula (I) is a compound having a high refractive index anisotropy Δn, the diffraction efficiency can be increased.

For the optical element, the description of [0067] to [0107] of WO2020/022496A can be referred to.

The optical element according to the embodiment of the present invention can be applied as an optical member such as an augmented reality (AR) image projection device.

Light Guide Element

A light guide element according to the embodiment of the present invention includes the above-described optical element and a light guide plate.

EXAMPLES

Hereinafter, the present invention will be described in detail with reference to Examples and Comparative Examples. In Examples below, the material, the using amount, the proportion, the details of treatment, the treatment procedure, and the like can be suitably modified without departing from the scope of the present invention. Accordingly, the scope of the present invention should not be interpreted restrictively by the following specific examples.

Examples of synthesis of compounds A-1 to A-20 are shown below. The structural formulae of the compounds A-1 to A-20 are as described above.

Synthesis Example 1: Synthesis of Compound A-1

The compound A-1 was synthesized according to the following scheme. It is noted that a compound 1 was synthesized according to WO2019/182129A, and the compound 6 was synthesized according to WO2007/140183A.

Ac represents an acetyl group, Ms represents a methanesulfonyl group ($-SO_2CH_3$), and TMS represents a trimethylsilyl group ($-Si(CH_3)_3$).

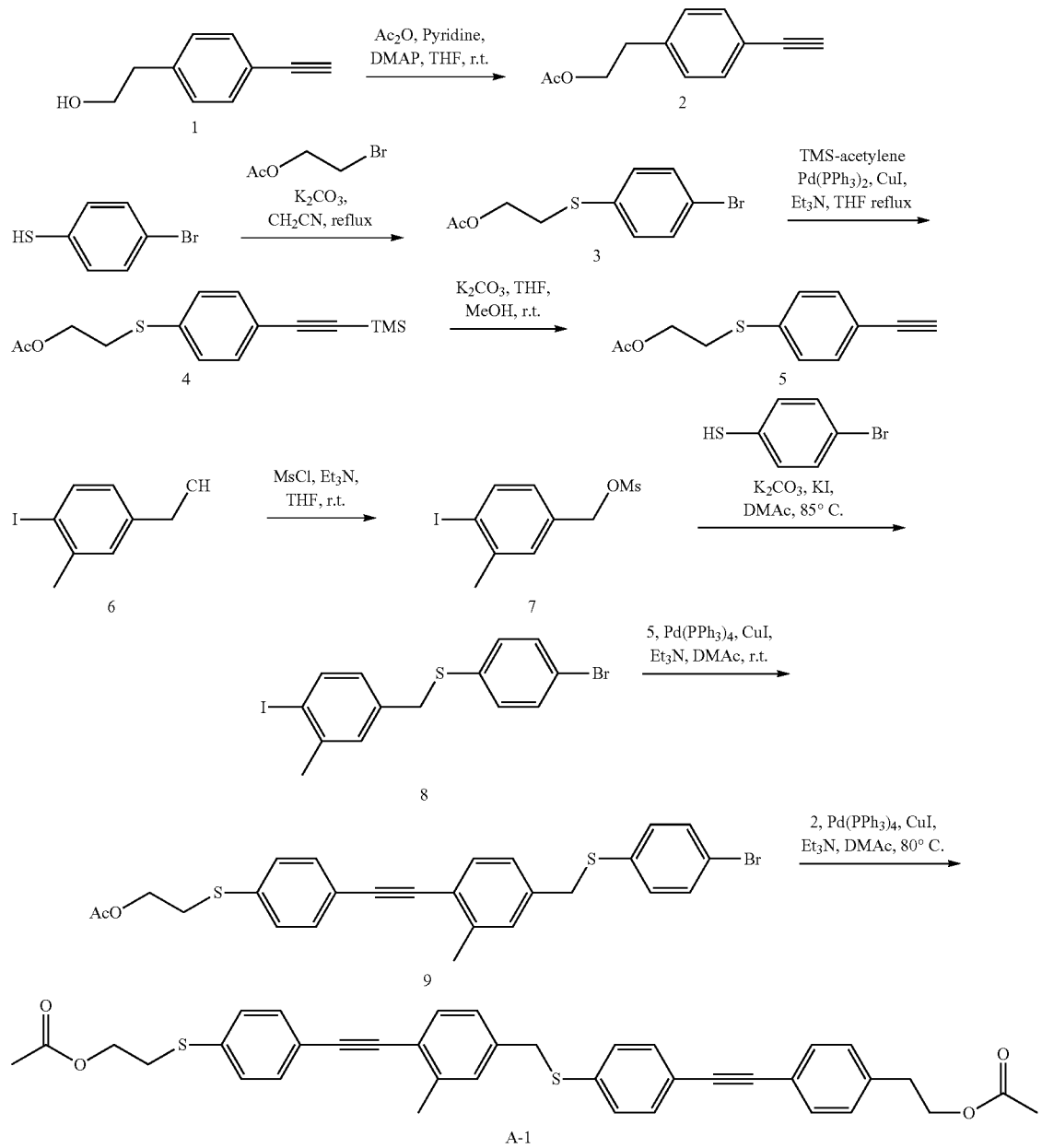

(1) Synthesis of Compound 2

The compound 1 (5.47 g, 35.5 mol) was dissolved in a mixed solution of tetrahydrofuran (THF) (30 mL) and pyridine (15 mL). The obtained solution was cooled in an ice water bath, acetic anhydride ($Ac_2O$) (5.44 g, 53.3 mmol) and 4-dimethylaminopyridine (DMAP) (0.43 g, 3.6 mmol) were added thereto, and stirring was carried out at room temperature (25° C.) for 3 hours. Ethyl acetate (50 mL) and water (50 mL) were added to the obtained solution, and then extraction was carried out with ethyl acetate. The obtained organic layer was washed with a saline solution and dried with magnesium sulfate. The organic layer was filtered, the solvent was distilled off under reduced pressure, and the obtained residue was purified by flash column chromatography, whereby a compound 2 (6.18 g, 32.8 mmol) was obtained. The yield was 92.4%.

(2) Synthesis of Compound 3

4-bromothiophenol (9.50 g, 50.3 mmol) and 2-bromoethyl acetate (8.39 g, 50.3 mmol) were dissolved in acetonitrile (100 mL), potassium carbonate (13.9 g, 100 mmol) was added thereto, and the resultant mixture was stirred with heating under reflux for 2 hours. The obtained solution was cooled to room temperature, ethyl acetate (100 mL) and 1 mol/L hydrochloric acid (200 mL) were added thereto, and then extraction was carried out with ethyl acetate. The obtained organic layer was sequentially washed with sodium bicarbonate solution and then a saline solution, dried with magnesium sulfate, and then the organic layer was filtered. The solvent was distilled off under reduced pressure, and the obtained residue was purified by flash column chromatography, whereby a compound 3 (12.6 g, 45.8 mmol) was obtained. The yield was 90.9%.

(3) Synthesis of Compound 4

The compound 3 (10.0 g, 36.3 mmol) was dissolved in THF (100 mL) in a nitrogen atmosphere, and triethylamine (36.8 g, 363 mmol) was added thereto. After nitrogen bubbling of the obtained solution for 1 hour, trimethylsilyl acetylene (3.93 g, 40.0 mmol), tetrakis(triphenylphosphine) palladium (0) ($Pd(PPh_3)_4$) (0.84 g, 0.73 mmol) and CuI (0.14 g, 0.73 mmol) were added thereto, and the resultant mixture was stirred with heating under reflux for 6 hours. The obtained solution was filtered and sequentially washed with water, 1 mol/L hydrochloric acid, sodium bicarbonate solution, and then a saline solution. The obtained organic layer was dried over Glauber's salt, and the organic layer was filtered. The solvent was distilled off under reduced pressure, and the obtained residue was purified by flash column chromatography, whereby a compound 4 (9.33 g, 31.9 mmol) was obtained. The yield was 79.2%.

(4) Synthesis of Compound 5

The compound 4 (8.39 g, 28.7 mmol) was dissolved in THF (50 mL). The obtained solution was cooled in an ice water bath, a THF solution of tetra-n-butylammonium fluoride (TBAF) (1 mol/L, 31.6 mL, 31.6 mmol) was added thereto, and stirring was carried out at room temperature for 2 hours. The obtained solution was cooled in an ice water bath, ethyl acetate (50 mL) and 1 mol/L hydrochloric acid (50 mL) were added thereto, and then extraction was carried out with ethyl acetate. The obtained organic layer was sequentially washed with water, sodium bicarbonate solution, and then a saline solution. The obtained organic layer was dried over Glauber's salt, and the organic layer was filtered. The solvent was distilled off under reduced pressure, and the obtained residue was purified by flash column chromatography, whereby a compound 5 (5.10 g, 23.2 mmol) was obtained. The yield was 80.7%.

(5) Synthesis of Compound 7

The compound 6 (4.49 g, 18.1 mmol) was dissolved in THF (20 mL). The obtained solution was cooled to −10° C., methanesulfonyl chloride (2.28 g, 19.9 mmol) and triethylamine (2.20 g, 21.7 mmol) were added thereto, and the resultant mixture was stirred at room temperature for 1 hour. The obtained solution was cooled in an ice water bath, ethyl acetate (70 mL) and water (20 mL) were added thereto, and then extraction was carried out with ethyl acetate. The obtained organic layer was washed with a saline solution and then dried with magnesium sulfate. After filtering the organic layer, the solvent was distilled off under reduced pressure, and the obtained residue was purified by flash column chromatography, whereby a compound 7 (5.70 g, 17.5 mmol) was obtained. The yield was 97.0%.

(6) Synthesis of Compound 8

The compound 7 (4.00 g, 12.3 mmol) and 4-bromothiophenol (2.32 g, 12.3 mmol) were dissolved in dimethylacetamide (DMAc) (30 mL), potassium carbonate (2.03 g, 14.7 mmol) and potassium iodide (0.20 g, 1.2 mmol) were added thereto, and the resultant mixture was stirred at 85° C. for 2 hours. The obtained solution was cooled to room temperature, ethyl acetate (100 mL) and water (50 mL) were added thereto, and then extraction was carried out with ethyl acetate. The obtained organic layer was sequentially washed with water and then a saline solution and then dried with magnesium sulfate. After filtering the organic layer, the solvent was distilled off under reduced pressure, and the obtained residue was purified by flash column chromatography, whereby a compound 8 (4.00 g, 9.5 mmol) was obtained. The yield was 77.5%.

(7) Synthesis of Compound 9

The compound 8 (2.30 g, 5.49 mmol) and the compound 5 (1.33 g, 6.04 mmol) were dissolved in THF (15 mL) in a nitrogen atmosphere, and triethylamine (5.55 g, 54.9 mmol) was added thereto. After nitrogen bubbling of the obtained solution for 20 minutes, $Pd(PPh_3)_4$ (0.32 g, 0.27 mmol) and CuI (0.11 g, 0.55 mmol) were added thereto, and the resultant mixture was stirred at room temperature for 1 hour. Ethyl acetate (100 mL) and water (30 mL) were added to the obtained solution, and then extraction was carried out with ethyl acetate. The obtained organic layer was sequentially washed with water and then a saline solution and then dried with magnesium sulfate. After filtering the organic layer, the solvent was distilled off under reduced pressure, and the obtained residue was purified by flash column chromatography, whereby a compound 9 (1.62 g, 3.17 mmol) was obtained. The yield was 57.7%.

(8) Synthesis of Compound A-1

The compound 9 (0.25 g, 0.40 mmol) and the compound 2 (0.22 g, 1.2 mmol) were dissolved in dimethylacetamide (DMAc) (5 mL) in a nitrogen atmosphere, and triethylamine (0.98 g, 9.7 mmol) was added thereto. After nitrogen bubbling of the obtained solution for 20 minutes, $Pd(PPh_3)_4$ (56 mg, 0.049 mmol) and CuI (19 mg, 0.097 mmol) were added thereto, and the resultant mixture was stirred at 80° C. for 4 hours. Ethyl acetate (20 mL) and water (20 mL) were added to the obtained solution, and then extraction was carried out with ethyl acetate. The obtained organic layer was washed with a saline solution and then dried with magnesium sulfate. After filtering the organic layer, the solvent was distilled off under reduced pressure, and the obtained residue was subjected to reslurry purification with MeOH, whereby the compound A-1 (0.25 g, 0.40 mmol) was obtained. The yield was 42%.

$^1$H-NMR (CDCl$_3$): δ=2.05 (s, 6H), 2.47 (s, 3H), 2.95 (t, 2H), 3.18 (t, 2H), 4.11 (s, 2H), 4.26 (t, 2H), 4.28 (t, 2H), 7.10 (d, 1H), 7.16-7.28 (m, 5H), 7.34 (d, 2H), 7.41 (d, 3H), 7.43-7.48 (m, 4H)

Synthesis Example 2: Synthesis of Compound A-2

The compound A-2 was synthesized according to the following scheme. It is noted that a compound 10 was synthesized from 4-iodobenzyl alcohol according to WO2019/182129A, and the compound 11 was synthesized according to J. Karsten, et al. Synthesis, 4, 539 (2011).

(2) Synthesis of Compound A-2

The compound 12 (1.50 g, 3.32 mmol) and the compound 5 (1.61 g, 7.30 mmol) were dissolved in DMAc (10 mL) in a nitrogen atmosphere, and triethylamine (3.36 g, 33.2 mmol) was added thereto. After nitrogen bubbling of the obtained solution for 20 minutes, Pd(PPh$_3$)$_4$ (0.19 g, 0.17 mmol) and CuI (0.06 g, 0.3 mmol) were added thereto, and the resultant mixture was stirred at room temperature for 4 hours. Ethyl acetate (10 mL) was added to the obtained solution, and the precipitate was filtered. The obtained solid

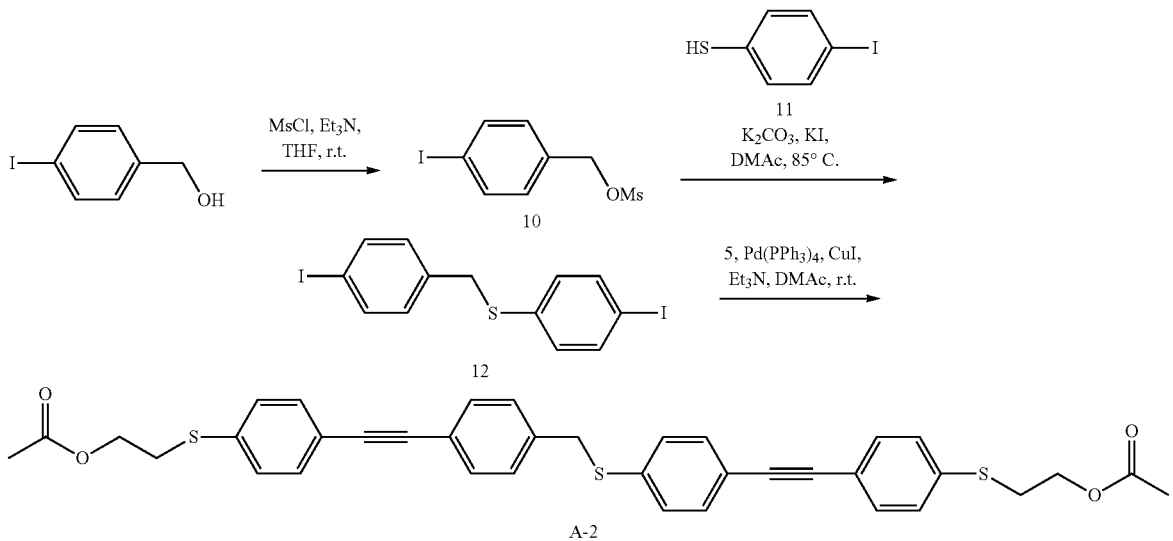

(1) Synthesis of Compound 12

The compound 10 (1.60 g, 5.13 mmol) and the compound 11 (1.21 g, 5.13 mmol) were dissolved in DMAc (10 mL), and potassium carbonate (0.85 g, 6.2 mmol) and potassium iodide (0.09 g, 0.5 mmol) were added thereto, and the resultant mixture was stirred at 85° C. for 2 hours. The obtained solution was cooled to room temperature, ethyl acetate (100 mL) and water (50 mL) were added thereto, and then extraction was carried out with ethyl acetate. The obtained organic layer was sequentially washed with water and then a saline solution and then dried with magnesium sulfate. After filtering the organic layer, the solvent was distilled off under reduced pressure, and the obtained residue was purified by flash column chromatography, whereby a compound 12 (1.93 g, 4.27 mmol) was obtained. The yield was 83.2%.

was subjected to reslurry washing with ethyl acetate to obtain the compound A-2 (1.52 g, 2.27 mmol). The yield was 68.300.

$^1$H-NM/R (CDCl$_3$): δ=2.04 (s, 6H), 3.18 (t, 4H), 4.13 (s, 2H), 4.26 (t, 4H), 7.22-7.30 (m, 4H), 7.33 (d, 4H), 7.39 (d, 2H), 7.42-7.47 (in, 6H)

Synthesis Example 3: Synthesis of Compound A-3

The compound A-3 was synthesized according to the following scheme. It is noted that A compound 16 was synthesized according to WO2011/050276, and a compound 13 was synthesized according to Chun, J. —H, et al. Org. Biomol. Chem. 11, 6300 (2013). TBS represents the tert-butyldimethylsilyl group.

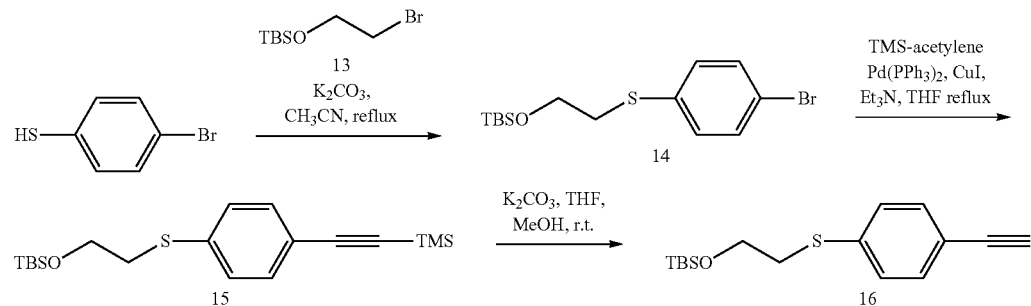

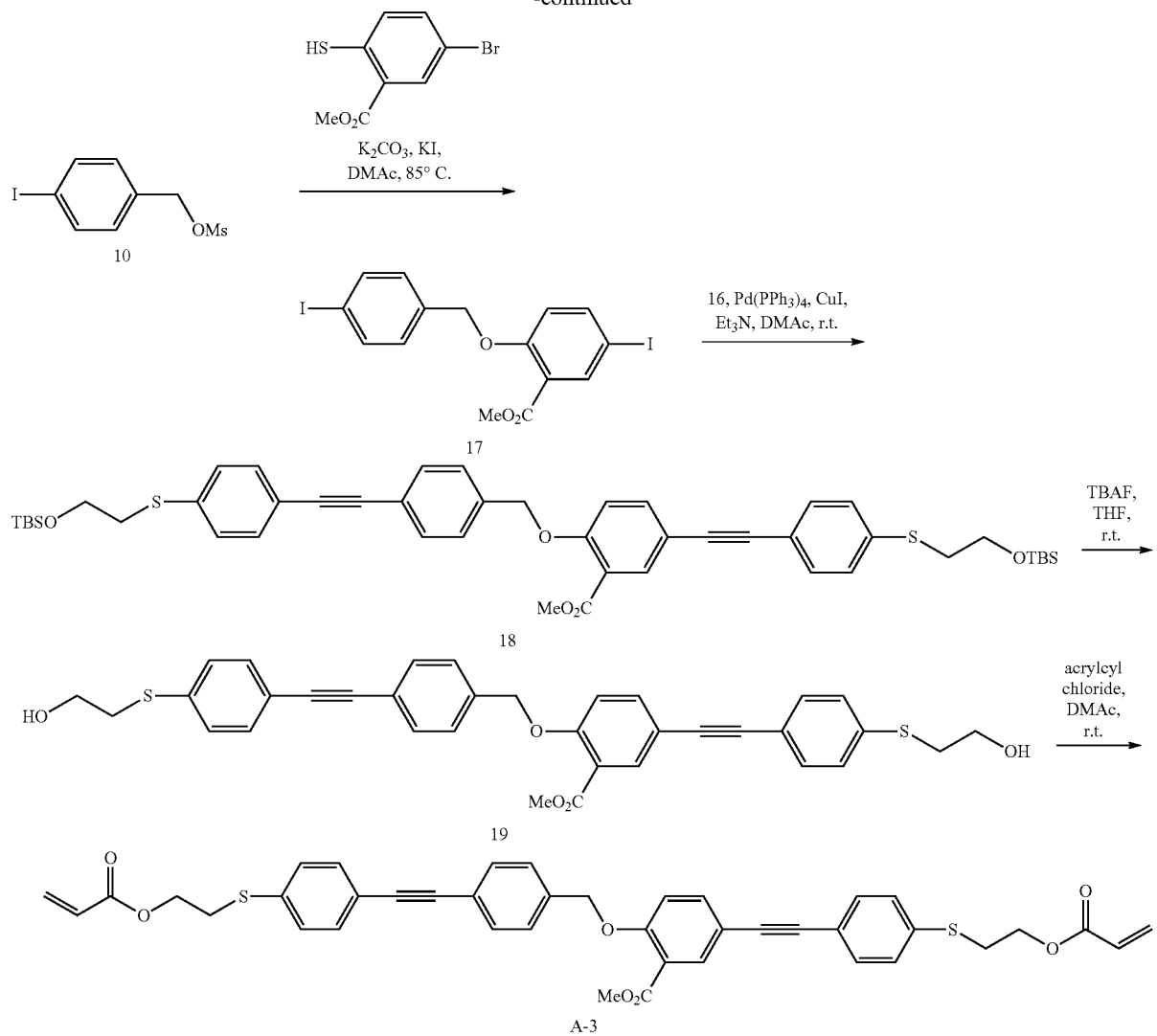

A-3

(1) Synthesis of Compound 14

4-bromothiophenol (28.0 g, 0.148 mol) and the compound 13 (36.5 g, 0.148 mmol) were dissolved in acetonitrile (500 mL), potassium carbonate (40.9 g, 0.296 mol) was added thereto, and the resultant mixture was stirred with heating under reflux for 2 hours. The obtained solution was cooled in an ice water bath, ethyl acetate (500 mL) and water (400 mL) were added thereto, and then extraction was carried out with ethyl acetate. The obtained organic layer was dried with magnesium sulfate, and the organic layer was filtered. The solvent was distilled off under reduced pressure, and the obtained residue was purified by flash column chromatography, whereby a compound 14 (52.2 g, 0.150 mol) was obtained. The yield was 62.4%.

(2) Synthesis of Compound 15

The compound 14 (32.0 g, 92.1 mmol) was dissolved in THF (320 mL) in a nitrogen atmosphere, and triethylamine (92.8 g, 0.917 mol) was added thereto. After nitrogen bubbling of the obtained solution for 1 hour, trimethylsilyl acetylene (10.9 g, 0.110 mol), Pd(PPh₃)₄ (2.12 g, 1.83 mmol) and CuI (0.35 g, 1.8 mmol) were added thereto, and the resultant mixture was stirred with heating under reflux for 4 hours. The obtained solution was filtered with celite and sequentially washed with water, 1 mol/L hydrochloric acid, sodium bicarbonate solution, and then a saline solution. The obtained organic layer was dried with magnesium sulfate, and the organic layer was filtered. The solvent was distilled off under reduced pressure, and the obtained residue was purified by flash column chromatography, whereby a compound 15 (28.4 g, 77.9 mmol) was obtained. The yield was 84.9%.

(3) Synthesis of Compound 16

The compound 15 (28.4 g, 77.9 mmol) was dissolved in a mixed solution of THF (140 mL) and methanol (MeOH) (140 mL), potassium carbonate (31.7 g, 0.229 mol) was added thereto, and the resultant mixture was stirred at room temperature for 1 hour. Water was added to the obtained solution, and then extraction was carried out with ethyl acetate. The obtained organic layer was washed with a saline solution and then dried with magnesium sulfate. After filtering the organic layer, the solvent was distilled off under reduced pressure, and the obtained residue was purified by flash column chromatography, whereby a compound 16 (20.5 g, 70.1 mmol) was obtained. The yield was 91.8%.

(4) Synthesis of Compound 17

The compound 10 (0.86 g, 2.8 mmol) and methyl 5-iodosalicylate (0.77 g, 2.8 mmol) were dissolved in DMAc (10 mL), and potassium carbonate (0.46 g, 3.3 mmol) and potassium iodide (0.05 g, 0.3 mmol) were added thereto, and the resultant mixture was stirred at 85° C. for 2 hours. Water (50 mL) was added to the obtained solution, and the precipitate was filtered to obtain a compound 17 (1.38 g, 2.76 mmol). The yield was 99.8%.

(5) Synthesis of Compound 18

The compound 17 (1.20 g, 2.43 mmol) and the compound 16 (1.56 g, 5.34 mmol) were dissolved in DMAc (10 mL) in a nitrogen atmosphere, and triethylamine (2.46 g, 24.3 mmol) was added thereto. After nitrogen bubbling of the obtained solution for 1 hour, Pd(PPh$_3$)$_4$ (0.14 mg, 0.12 mmol) and CuI (47 mg, 0.24 mmol) were added thereto, and the resultant mixture was stirred at room temperature for 2 hours. The obtained solution was cooled in an ice water bath, ethyl acetate (50 mL) and water (20 mL) were added thereto, and then extraction was carried out with ethyl acetate. The obtained organic layer was sequentially washed with water and then a saline solution and then dried with magnesium sulfate. After filtering the organic layer, the solvent was distilled off under reduced pressure, and the obtained residue was purified by flash column chromatography, whereby a compound 18 (1.83 g, 2.22 mmol) was obtained. The yield was 91.5%.

(6) Synthesis of Compound 19

The compound 18 (1.83 g, 2.22 mmol) was dissolved in THF (15 mL). The obtained solution was cooled in an ice water bath, a THF solution of TBAF (1 mol/L, 4.7 mL, 4.7 mmol) was added thereto, and stirring was carried out at room temperature for 1 hour. The obtained solution was cooled in an ice water bath, chloroform (50 mL) and water (20 mL) were added thereto, and then extraction was carried out with chloroform. The obtained organic layer was washed with a saline solution and then dried with magnesium sulfate. After filtering the organic layer, the solvent was distilled off under reduced pressure, and the obtained residue was purified by flash column chromatography, whereby a compound 19 (1.22 g, 1.97 mmol) was obtained. The yield was 88.5%.

(7) Synthesis of Compound A-3

The compound 19 (1.22 g, 2.05 mmol) was dissolved in DMAc (5 mL). The obtained solution was cooled in an ice water bath, acryloyl chloride (0.63 g, 7.0 mmol) was added thereto, and stirring was carried out at room temperature for 1 hour. Ethyl acetate (50 mL) and water (20 mL) were added to the obtained solution, and then extraction was carried out with ethyl acetate. The obtained organic layer was sequentially washed with water, sodium bicarbonate solution, and then a saline solution, and then dried with magnesium sulfate. After filtering the organic layer, the solvent was distilled off under reduced pressure, and the obtained residue was purified by flash column chromatography, whereby the compound A-3 (1.05 g, 1.49 mmol) was obtained. The yield was 72.8%.

$^1$H-NMR (CDCl$_3$): δ=3.221 (t, 2H), 3.226 (t, 2H), 4.350 (t, 2H), 4.352 (t, 2H), 5.23 (s, 2H), 5.848 (d, 1H), 5.850 (d, 1H), 6.094 (dd, 1H), 6.097 (dd, 1H), 6.40 (d, 2H), 6.98 (d, 1H), 7.32-7.38 (m, 4H), 7.40-7.51 (m, 6H), 7.53-7.60 (m, 3H), 8.02 (d, 1H)

Synthesis Example 4: Synthesis of Compound A-4

The compound A-4 was obtained according to the same procedure as in Synthesis Example 3, except that the compound 20 obtained by subjecting methyl 5-iodosalicylate and 4-iodobenzoic acid to esterification was used instead of the compound 17.

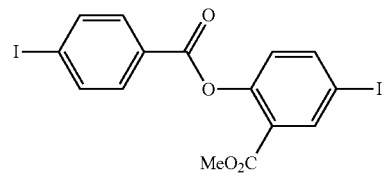

Synthesis Example 5: Synthesis of Compound A-5

The compound A-5 was obtained according to the same procedure as in Synthesis Example 3, except that 4-bromo-3-methoxybenzyl alcohol synthesized according to Gilmartin, P. H. et al. Org. Lett. 22, 2914 (2020) was used instead of the compound 10, and the compound 11 was used instead of methyl 5-iodosalicylate.

Synthesis Example 6: Synthesis of Compound A-6

The compound A-6 was obtained according to the same procedure as in Synthesis Example 3, except that 2-methyl-4-iodophenol was used instead of methyl 5-iodosalicylate.

Synthesis Example 7: Synthesis of Compound A-7

The compound A-7 was obtained according to the same procedure as in Synthesis Example 3, except that 4-bromo-2-fluorophenol was used instead of methyl 5-iodosalicylate.

Synthesis Example 8: Synthesis of Compound A-8

The compound A-8 was obtained according to the same procedure as in Synthesis Example 3, except that the compound 21 was synthesized according to Chun, J.-H, et al. Org. Biomol. Chem. 11, 6300 (2013) was used instead of 4-iodobenzyl alcohol, which is the raw material of the compound 10.

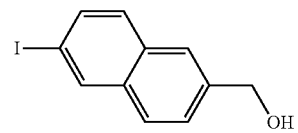

Synthesis Example 9: Synthesis of Compound A-9

The compound A-9 was obtained according to the same procedure as in Synthesis Example 3, except that the compound 21 was used instead of 4-iodobenzyl alcohol, which is the raw material of the compound 10, and ethyl 5-iodosalicylate synthesized according to Narges, H.-E. et al. Bioorg, Med. Chem. Lett. 17, 6354 (2007) was used instead of methyl 5-iodosalicylate.

Synthesis Example 10: Synthesis of Compound A-10

The compound A-10 was obtained according to the same procedure as in Synthesis Example 3, except that the compound 21 was used instead of 4-iodobenzyl alcohol, and 4-iodo-2,6-dimethylphenol was used instead of methyl 5-iodosalicylate.

Synthesis Example 11: Synthesis of Compound A-11

The compound A-11 was obtained according to the same procedure as in Synthesis Example 3, except that methyl 7-bromo-3-hydroxy-2-naphthoate synthesized according to T. Aoyama, Chem. Pharm. Bull. 33, 1458 (1985) was used instead of methyl 5-iodosalicylate.

Synthesis Example 12: Synthesis of Compound A-12

The compound A-12 was obtained according to the same procedure as in Synthesis Example 3, except that 4-(4-bromophenyl)benzyl alcohol synthesized according to EP2407502B was used instead of 4-iodobenzyl alcohol.

Synthesis Example 13: Synthesis of Compound A-13

The compound A-13 was obtained according to the same procedure as in Synthesis Example 1, except that 4-iodophenol was used instead of 4-bromothiophenol.

Synthesis Example 14: Synthesis of Compound A-14

The compound A-14 was synthesized according to the same procedure as in Synthesis Example 3, except that a compound 22 synthesized according to the following scheme was used instead of the compound 17.

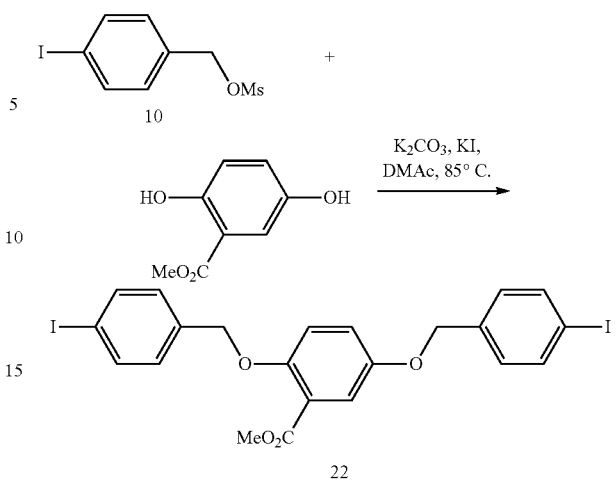

(1) Synthesis of Compound 22

The compound 10 (3.00 g, 9.61 mmol) and methyl 2,5-dihydroxybenzoate (0.81 g, 4.86 mmol) were dissolved in DMAc (20 mL), potassium carbonate (1.59 g, 11.5 mmol) and potassium iodide (0.16 g, 0.96 mmol) were added thereto, and the resultant mixture was stirred at 85° C. for 3 hours. The obtained solution was cooled to room temperature, water (100 mL) was added thereto, and the precipitate was filtered. The obtained solid was purified by flash column chromatography to obtain the compound 22 (1.81 g, 3.02 mmol). The yield was 62.8%.

Synthesis Example 15: Synthesis of Compound A-15

The compound A-15 was synthesized according to the following scheme. Ac represents an acetyl group.

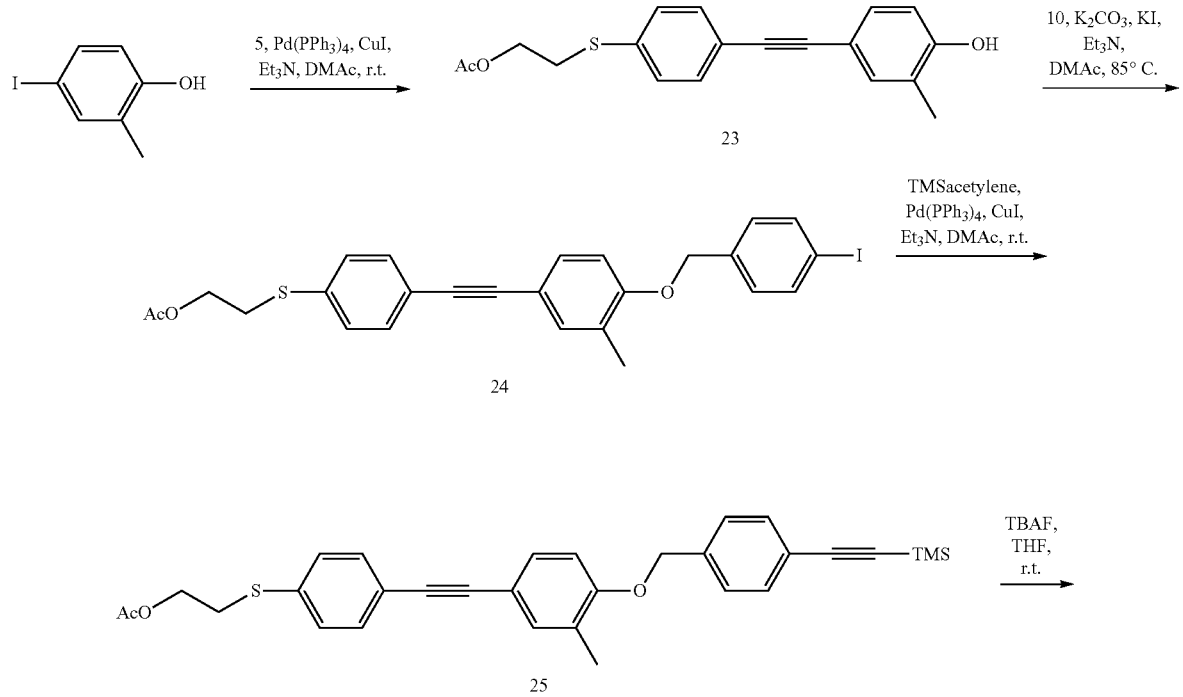

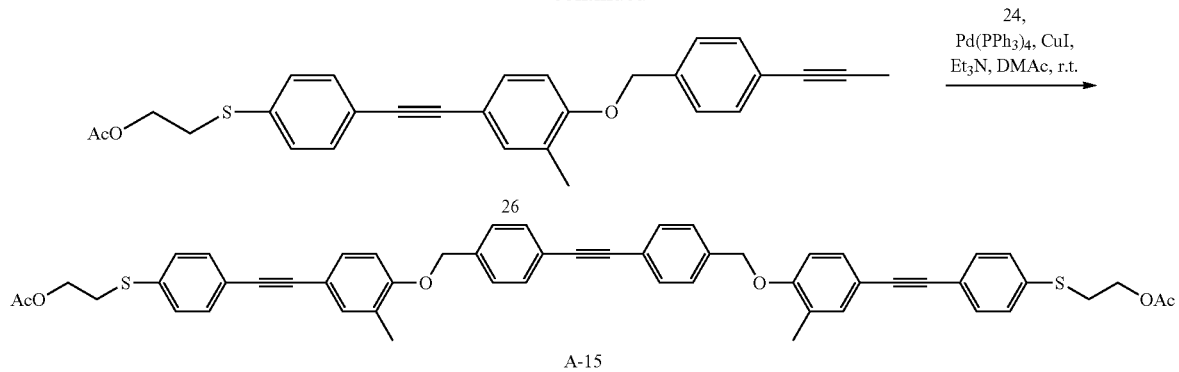

A-15

(1) Synthesis of Compound 23

2-methyl-4-iodophenol (1.60 g, 6.84 mol) and the compound 5 (1.81 g, 8.20 mmol) were dissolved in THF (10 mL) in a nitrogen atmosphere, and triethylamine (6.92 g, 68.4 mmol) was added thereto. After nitrogen bubbling of the obtained solution for 1 hour, Pd(PPh$_3$)$_4$ (0.40 g, 0.34 mmol) and CuI (0.13 g, 0.68 mmol) were added thereto, and the resultant mixture was stirred at room temperature for 1 hour. Ethyl acetate (30 mL) was added to the obtained solution, and filtration was carried out. Water (30 mL) was added to the obtained solution, and then extraction was carried out with ethyl acetate. The obtained organic layer was sequentially washed with water, 1 mol/L hydrochloric acid, and then a saline solution, and then dried with magnesium sulfate. After filtering the organic layer, the solvent was distilled off under reduced pressure, and the obtained residue was purified by flash column chromatography, whereby a compound 18 (2.15 g, 6.59 mmol) was obtained. The yield was 96.4%.

(2) Synthesis of Compound 24

The compound 23 (0.77 g, 2.4 mmol) and the compound 10 (0.74 g, 2.4 mmol) were dissolved in DMAc (15 mL), and potassium carbonate (0.39 g, 2.9 mmol) and potassium iodide (0.04 g, 0.3 mmol) were added thereto, and the resultant mixture was stirred at 85° C. for 2 hours. The obtained solution was cooled to room temperature, ethyl acetate (70 mL) and water (50 mL) were added thereto, and then extraction was carried out with ethyl acetate. The obtained organic layer was sequentially washed with water and then a saline solution and then dried with magnesium sulfate. After filtering the organic layer, the solvent was distilled off under reduced pressure, and the obtained residue was subjected to reslurry washing with a mixed solvent of ethyl acetate and hexane to obtain a compound 24 (0.87 g, 1.6 mmol). The yield was 68%.

(3) Synthesis of Compound 25

The compound 24 (0.43 g, 0.78 mmol) was dissolved in THF (5 mL) in a nitrogen atmosphere, and triethylamine (0.79 g, 7.8 mmol) was added thereto. After nitrogen bubbling of the obtained solution from 20 minutes, tetramethylsilyl acetylene (0.13 mL, 0.94 mmol), Pd(PPh$_3$)$_4$ (45.3 mg, 0.0392 mmol), and CuI (15.0 g, 0.0784 mmol) were added thereto, and the resultant mixture was stirred at room temperature for 1 hour. Ethyl acetate (30 mL) and water (10 mL) were added to the obtained solution, and then extraction was carried out with ethyl acetate. The obtained organic layer was washed with a saline solution, dried with magnesium sulfate, and the organic layer was filtered. The solvent was distilled off under reduced pressure, and the obtained residue was purified by flash column chromatography, whereby a compound 25 (0.39 g, 0.76 mmol) was obtained. The yield was 97%.

(4) Synthesis of Compound 26

The compound 25 (0.39 g, 0.76 mmol) was dissolved in THF (5 mL). The obtained solution was cooled in an ice water bath, a THF solution of TBAF (1 mol/L, 0.86 mL, 0.86 mmol) was added thereto, and stirring was carried out at room temperature for 1 hour. Ethyl acetate (30 mL) and water (10 mL) were added to the obtained solution, and then extraction was carried out with ethyl acetate. The obtained organic layer was washed with a saline solution and then dried with magnesium sulfate. After filtering the organic layer, the solvent was distilled off under reduced pressure, and the obtained residue was purified by flash column chromatography, whereby a compound 26 (0.33 g, 0.75 mmol) was obtained. The yield was 99%.

(5) Synthesis of Compound A-15

The compound 24 (0.40 g, 0.73 mmol) and the compound 26 (0.35 g, 0.80 mmol) were dissolved in THF (5 mL) in a nitrogen atmosphere, and triethylamine (0.73 g, 7.3 mmol) was added thereto. After nitrogen bubbling of the obtained solution for 1 hour, Pd(PPh$_3$)$_4$ (42 mg, 0.036 mmol) and CuI (14 mg, 0.073 mmol) were added thereto, and the resultant mixture was stirred at room temperature for 1 hour. After adding chloroform (30 mL) to the obtained solution, the solvent was distilled off under reduced pressure, and the obtained residue was purified by flash column chromatography to obtain the compound A-15 (0.24 g, 0.28 mmol). The yield was 39%.

$^1$H-NMR (CDCl$_3$): δ=2.04 (s, 6H), 2.30 (s, 6H), 3.18 (t, 4H), 4.26 (t, 4H), 5.13 (br s, 4H), 6.80-6.85 (m, 2H), 7.17-7.21 (m, 2H), 7.31-7.38 (m, 4H), 7.40-7.47 (m, 8H), 7.54-7.59 (m, 2H)

Synthesis Example 16: Synthesis of Compound A-16

The compound A-16 was obtained according to the same procedure as in Synthesis Example 3, except that 5-bromo-thiophene-2-yl methanol was synthesized according to Lee, J. et al. J. Org. Chemm. 77, 4821 (2012) was used instead of 4-iodobenzyl alcohol.

Synthesis Example 17: Synthesis of Compound A-17

The compound A-17 was synthesized according to the same procedure as in Synthesis Example 3, except that 2-methyl-4-iodophenol was used instead of 4-bromothiophenol and the compound 27 synthesized according to the following scheme was used instead of the compound 17.

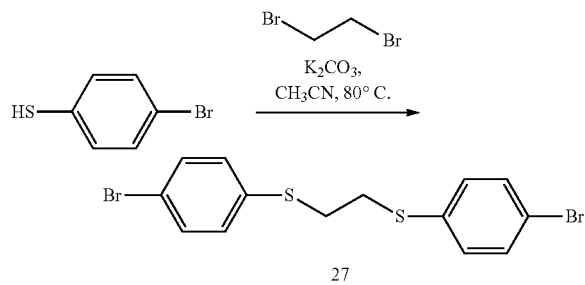

(1) Synthesis of Compound 27

4-bromothiophenol (11.3 g, 59.8 mmol) and 1,2-dibromoethane (5.63 g, 30.0 mmol) were dissolved in acetonitrile (150 mL), potassium carbonate (16.6 g, 120 mmol) was added thereto, and the resultant mixture was stirred at 80° C. for 2 hours. The obtained solution was cooled to room temperature, ethyl acetate (50 mL) and water (50 mL) were added thereto, and the precipitate was filtered to obtain a compound 27 (4.62 g, 11.4 mmol). The yield was 38.1%.

Synthesis Example 18: Synthesis of Compound A-18

The compound A-18 was synthesized according to the same procedure as in Synthesis Example 3, except that the compound 28 synthesized according to the following scheme was used instead of the compound 17.

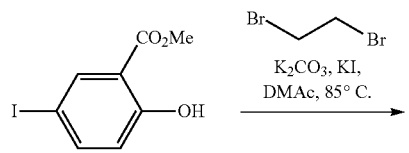

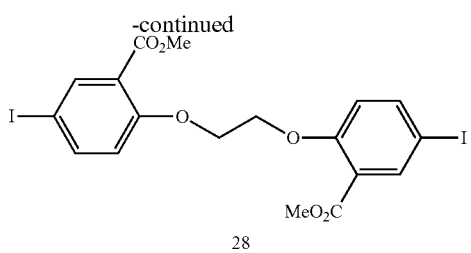

(1) Synthesis of Compound 28

Methyl 5-iodosalicylate (8.88 g, 31.9 mmol) and 1,2-dibromoethane (3.00 g, 16.0 mmol) were dissolved in DMAc (30 mL), potassium carbonate (5.30 g, 38.3 mmol) and potassium iodide (0.27 g, 0.16 mmol) were added thereto, and the resultant mixture was stirred at 85° C. for 3 hours. The obtained solution was cooled to room temperature, water (100 mL) was added thereto, and the precipitate was filtered. The obtained solid was subjected to reslurry washing with ethyl acetate, dissolved in chloroform, and subjected to the reprecipitation treatment by adding MeOH, whereby a compound 28 (2.99 g, 5.14 mmol) was obtained. The yield was 32.2%.

Synthesis Example 19: Synthesis of Compound A-19

The compound A-19 was obtained according to the same procedure as in Synthesis Example 3, except that 3-bromopropanol was used instead of 2-bromoethanol, which is the raw material of the compound 13.

Synthesis Example 20: Synthesis of Compound A-20

The compound A-20 was obtained according to the same procedure as in Synthesis Example 3, except that 4-bromobutanol was used instead of 2-bromoethanol, which is the raw material of the compound 13.

Synthesis of Compound RA-1

A compound RA-1 was synthesized as a comparative compound according to Synthesis Example 1 of JP2005-15406A.

Synthesis of Compound RA-2

A compound RA-2 was obtained as a comparative compound according to WO2018/034216A.

RA-1

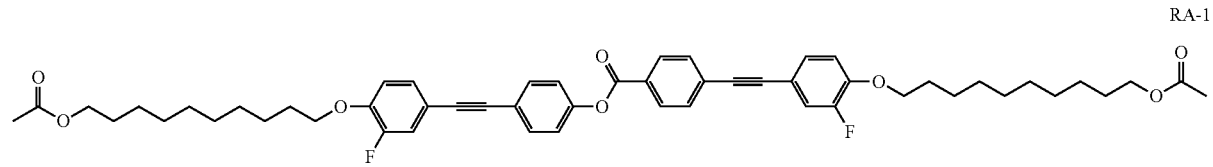

RA-2

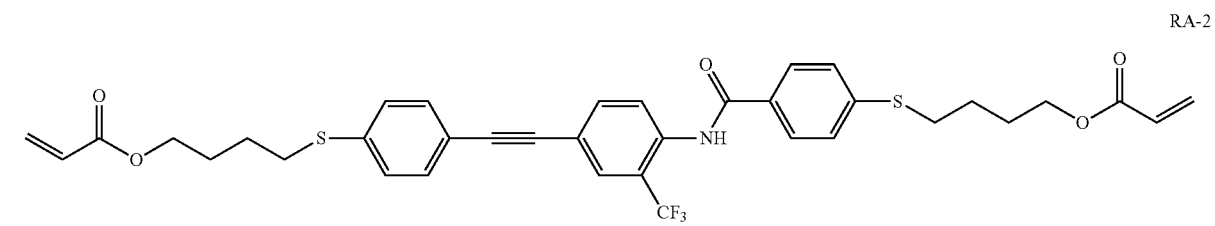

Examples 1 to 19 and Comparative Examples 1 and 2

Evaluation

As Examples 1 to 19, the compounds A-1 and A-3 to A-20 were respectively used, and the evaluation described below was carried out. Further, as Comparative Examples 1 and 2, the respective compounds RA-1 and RA-2 we7re used, and the evaluation described below was carried out.

Evaluation of Liquid Crystallinity

The respective compounds of Examples and Comparative Examples (the compounds A-1, A-3 to A-20, and the compounds RA-1 and RA-2) were heated on a hot stage and observed with a polarization microscope, and the phase transition temperature was measured to evaluate the presence or absence of liquid crystallinity. A case of having liquid crystallinity was evaluated as A, and a case of having no liquid crystallinity was evaluated as B. The results are shown in Table 1.

Measurement of Δn (Refractive Index Anisotropy)

The Δn of each of the compounds of Examples and Comparative Examples (the compounds A-1, A-3 to A-20, and the compounds RA-1 and RA-2), which are the compounds to be measured, was measured by a method using a wedge-shaped liquid crystal cell described on page 202 in the Liquid crystal handbook (edited by the liquid crystal handbook editorial board, published by Maruzen Co., Ltd., 2000). Δn was defined as a measured value at a wavelength of 550 nm at 30° C. or the lower limit temperature of the nematic phase+0° C. to 10° C. In a case of a compound which is liable to crystallize or a compound having no liquid crystallinity, evaluation was carried out using a mixture thereof with the other liquid crystal compound, and Δn was estimated from the extrapolated value of the measured value thereof. The following L-1-1 was used as the other liquid crystal compound. As the above mixture, a mixture obtained by mixing at a ratio of the compound to be measured/the L-1-1=1/2 (in terms of mass ratio) was used.

A case where Δn was 0.35 or more was evaluated as A, a case where Δn was 0.32 or more and less than 0.35 was evaluated as B, a case where Δn was 0.30 or more and less than 0.32 was evaluated as C, and a case where Δn was less than 0.30 was evaluated as D. The results are shown in Table 1.

Evaluation of Solubility

The solubility of each of the compounds of Examples and Comparative Examples (the compounds A-1, A-3 to A-20, and the compounds RA-1 and RA-2) in methyl ethyl ketone was evaluated. A solution in which the compound was ultrasonically dissolved or dissolved by heating was produced. Thereafter, it was observed at room temperature (25° C.) whether or not the compound was precipitated in the solution. Solutions were prepared at various concentrations for each compound, the concentration at which precipitation occurred was defined as the precipitation concentration, the solubility in a case where the precipitation concentration was 10% by mass or more was evaluated as A, and the solubility in a case where the precipitation concentration was less than 10% by mass was evaluated as B. The results are shown in Table 1.

Evaluation of Light Resistance/Durability

As shown below, the durability of the optically anisotropic layer produced using the composition containing each of the compounds A-1 and A-3 to A-20, and the compounds RA-1 and RA-2 was evaluated.

Production of Optically Anisotropic Layer for Light Resistance/Durability Test

A coating composition having the following composition was prepared and applied by spin coating onto a rubbing-treated glass attached with an alignment film. Each coating composition was irradiated with ultraviolet rays of 300 mJ/cm$^2$ through a filter that cuts light having a wavelength of 350 nm or less on a hot plate heated to a temperature at which a nematic phase was exhibited, whereby optically anisotropic layers for light resistance/durability tests (an optically anisotropic layer for a light resistance test and an optically anisotropic layer for a durability test) was produced.

| Composition of coating composition | |
|---|---|
| The compound of each of Examples and Comparative Examples shown in Table 1 below | 25 parts by mass |
| The following polymerizable liquid crystal compound L-1 | 75 parts by mass |
| A polymerization initiator (Irgacure (registered trade name) 907, manufactured by BASF SE) | 2 parts by mass |
| The following leveling agent T-1 | 0.1 parts by mass |
| Chloroform | 1,940 parts by mass |

The polymerizable liquid crystal compound L-1 is a mixture obtained by mixing at a ratio of the following L-1-1/L-1-2/L-1-3=84/14/2 (in terms of mass ratio).

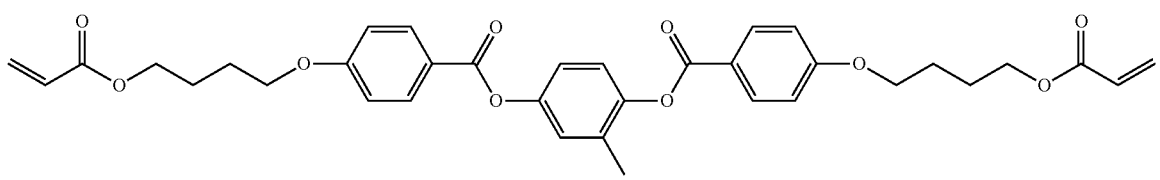

L-1-1

L-1

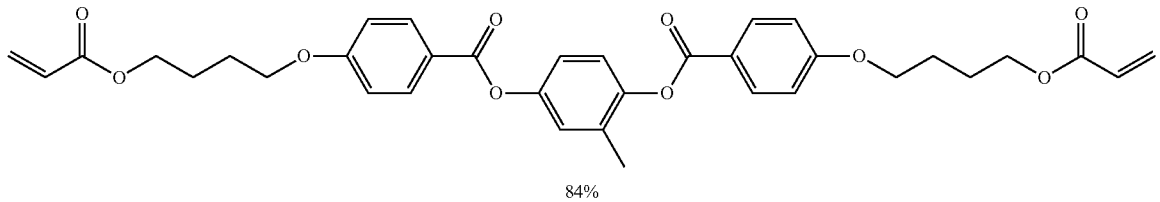

L-1-1

84%

L-1-2

14%

L-1-3

2%

The leveling agent T-1 is a compound having the following structure.

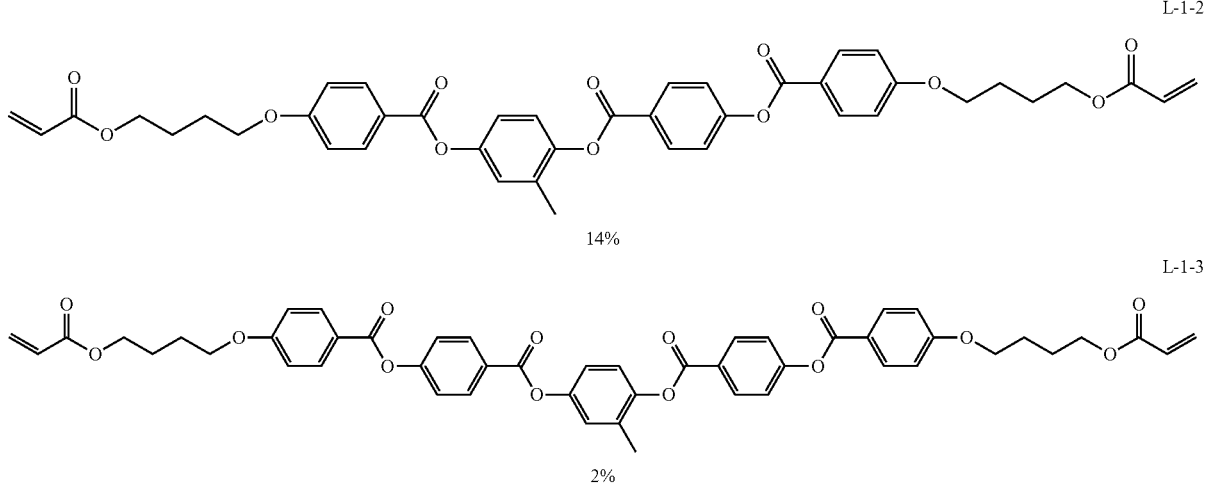

T-1

Evaluation of Light Resistance

The produced optically anisotropic layers for light resistance/durability tests were irradiated with light using a Super Xenon Weather Meter SX75 manufactured by Suga Test Instruments Co., Ltd. Using KU-1000100 manufactured by King Seisakusho Co., Ltd. as an ultraviolet ray cut filter, irradiation with 5 million 1× of light was carried out for 50 hours under the oxygen-blocking conditions to carry out a light resistance test. The temperature of the specimen to be tested (the temperature inside the test device) was set to 63° C. The relative humidity in the test device was 50% RH.

The Re of the optically anisotropic layer before and after the light resistance test was measured, the light resistance in a case where the rate of change in Re described below was less than 10% was evaluated as A, and the light resistance in a case where the rate of change in Re was 10% or more was evaluated as B. The smaller the rate of change in Re, the more excellent the light resistance. The results are shown in Table 1.

Re is an in-plane retardation.

Rate of change in Re (%)=[100×{|(Re after test)−(Re before test)|}/(Re before test)]

Re was measured with Axoscan manufactured by Axometrics, Inc. at a wavelength of 550 nm, and the measurement temperature was set to room temperature.

Evaluation of Durability

The produced optically anisotropic layer was allowed to be left for 136 hours at 100° C. and a relative humidity of 95% RH, whereby a moisture-heat resistance test was carried out. The rate of change in Re before and after the durability test was evaluated, the durability in a case where the rate of change in Re was less than 10% was evaluated as A, and the durability in a case where the rate of change in Re was 10% or more was evaluated as B. The smaller the rate of change in Re, the more excellent the durability. The results are shown in Table 1.

Example 20

As Example 20, an optical element was produced using the compound A-9 as shown below.

Production of Optical Element

Preparation of support and saponification treatment of support

As the support, a commercially available triacetyl cellulose film (manufactured by FUJIFILM Corporation, Z-TAC) was prepared.

The support was allowed to pass through a dielectric heating roll at a temperature of 60° C. so that the surface temperature of the support was increased to 40° C.

Next, an alkali solution described below was applied onto a single surface of the support using a bar coater in a coating amount of 14 mL (liter)/m², the support was heated to 110° C., and the support was transported for 10 seconds under a steam-type far infrared heater (manufactured by Noritake Co., Ltd.).

Subsequently, 3 mL/m² of pure water was applied onto the surface of the support, onto which the alkali solution had been applied, using the same bar coater. Next, water cleaning using a foundry coater and water draining using an air knife were repeated three times, and then the support was transported and dried in a drying zone at 70° C. for 10 seconds, whereby the surface of the support was subjected to the alkali saponification treatment.

| Alkali solution | |
|---|---|
| Potassium hydroxide | 4.70 parts by mass |
| Water | 15.80 parts by mass |
| Isopropyl alcohol | 63.70 parts by mass |
| A surfactant SF-1: ($C_{14}H_{29}O(CH_2CH_2O)_2OH$) | 1.0 part by mass |
| Propylene glycol | 14.8 parts by mass |

Formation of Undercoat Layer

The following coating liquid for forming an undercoat layer was continuously applied onto the surface of the support, which had been subjected to the alkali saponification treatment, using a #8 wire bar. The support on which the coating film had been formed was dried using warm air at 60° C. for 60 seconds and further dried using warm air at 100° C. for 120 seconds to form an undercoat layer.

| Coating liquid for forming undercoat layer | |
|---|---|
| The following modified polyvinyl alcohol | 2.40 parts by mass |
| Isopropyl alcohol | 1.60 parts by mass |
| Methanol | 36.00 parts by mass |
| Water | 60.00 parts by mass |

Modified polyvinyl alcohol (the ratios of repeating units in the following structural formula is in terms of mass ratio)

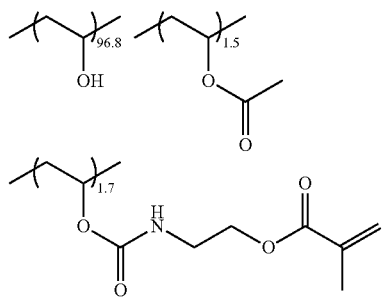

Formation of Alignment Film

The following coating liquid for forming an alignment film was continuously applied onto the support, onto which the undercoat layer had been formed, using a #2 wire bar. The support on which the coating film of the coating liquid for forming an alignment film had been formed was dried using a hot plate at 60° C. for 60 seconds to form an alignment film.

| Coating liquid for forming alignment film | |
|---|---|
| A material D for photo alignment | 1.00 part by mass |
| Water | 16.00 parts by mass |
| Butoxyethanol | 42.00 parts by mass |
| Propylene glycol monomethyl ether | 42.00 parts by mass |

The material D for photo alignment is a compound having the following structure.

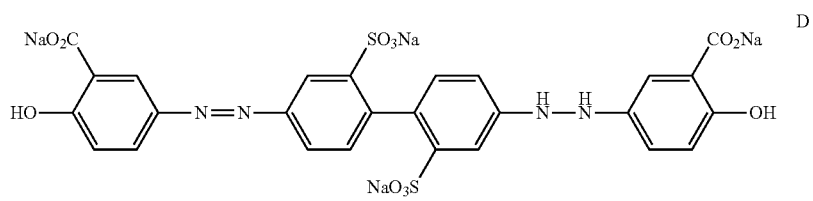

Exposure of Alignment Film

The alignment film was exposed using the exposure device of FIG. 5 of WO2020/22496A to form an alignment film P-1 having an alignment pattern.

In the exposure device, a laser that emits a laser beam having a wavelength of 325 nm was used as the laser. The exposure amount of the interference light was 2,000 mJ/cm². It is noted that one period (the length over which the optical axis derived from the liquid crystal compound rotates 180°) of an alignment pattern formed by interference of two laser beams was controlled by changing the intersecting angle (the intersecting angle 3) between the two beams.

Formation of Optically Anisotropic Layer

As a composition for forming an optically anisotropic layer, the following composition E-1 was prepared.

| Composition E-1 | |
|---|---|
| A liquid crystal compound A-9 | 100.00 parts by mass |
| A polymerization initiator (Irgacure (registered trade name) 907, manufactured by BASF SE) | 3.00 parts by mass |

| Composition E-1 | |
|---|---|
| The above leveling agent T-1 | 0.08 parts by mass |
| Methyl ethyl ketone | 927.7 parts by mass |

An optically anisotropic layer was formed by subjecting the alignment film P-1 to multilayer coating with the composition E-1. Here, the multilayer coating refers to the repetition of the process of producing a liquid crystal immobilized layer by applying the composition E-1 for a first layer onto the alignment film, followed by heating, cooling, and then curing with an ultraviolet ray; and then subjecting the liquid crystal immobilized layers to repeat coating for second and subsequent layers, followed by the same heating, cooling, and then curing with an ultraviolet ray as described above. Due to the formation by the multilayer coating, the alignment direction of the alignment film is reflected over the upper surface of the liquid crystal layer from the lower surface (the surface on the alignment film P-1 side) even in a case where the film thickness of the liquid crystal layer is increased.

Regarding the first liquid crystal layer, the above-described composition E-1 was applied to the alignment film P-1 to form a coating film, the coating film was heated using a hot plate at 80° C., the coating film was cooled to 50° C., and the coating film was irradiated with ultraviolet rays having a wavelength of 365 nm at an irradiation dose of 300 mJ/cm$^2$ using a high-pressure mercury lamp in a nitrogen atmosphere. As a result, the alignment of the liquid crystal compound was immobilized. At this time, the film thickness of the first liquid crystal layer was 0.3 m.

This liquid crystal layer was subjected to repeat coating for the second and subsequent liquid crystal layers, followed by heating, cooling, and then curing with an ultraviolet ray under the same conditions as described above to produce a liquid crystal immobilized layer (a cured layer). In this way, the repeat coating was repeated until the retardation reached 325 nm, an optically anisotropic layer was formed, and then an optical element G-1 was produced.

Using a polarization microscope, it was confirmed that the optically anisotropic layer of this example had a periodic alignment surface as shown in FIG. 3 of WO2020/22496A. In the alignment pattern of the optically anisotropic layer, the one period A over which the optical axis derived from the liquid crystal compound A-9 rotated 180° was 1.0 µm. The period A was determined by measuring the period of the bright and dark pattern observed under the crossed nicol condition using a polarization microscope.

Measurement of Diffraction Efficiency

An evaluation optical system in which a light source for evaluation, a polarizer, a ¼ wavelength plate, the optical element G-1, and a screen were arranged in this order was prepared. A laser pointer having a wavelength of 650 nm was used as the light source for evaluation, and SAQWP05M-700 manufactured by Thorlabs Inc. was used as the ¼ wavelength plate. The slow axis of the ¼ wavelength plate was arranged at a relationship of 45° with respect to the absorption axis of the polarizer. In addition, the optical element G-1 was arranged so that the support surface faced the light source side.

When the light transmitted from the light source for evaluation through the polarizer and the ¼ wavelength plate became incident on the optical element G-1 with being perpendicular to the film surface, a part of the light transmitted through the optical element G-1 was diffracted, and a plurality of bright spots were confirmed on the screen.

The intensity of the diffracted light corresponding to each of the bright spots on the screen and the intensity of the 0th light were measured with a power meter, and the diffraction efficiency was calculated according to the following expression.

Diffraction efficiency=(intensity of 1st light)/(intensity of 0th light+intensity of diffracted light other than 1st light)

The obtained diffraction efficiency was as high as 99% or more.

Liquid Crystallinity of Composition

When the composition E-1 was dried and the solvent (methyl ethyl ketone) was volatilized, it was confirmed that liquid crystallinity was exhibited.

Example 21

As Example 21, a light guide element was produced using a composition containing the compound A-9 and a chiral agent, as shown below.

The following composition E-2 was prepared as a composition for forming a cholesteric liquid crystal layer as shown in FIG. 6 of WO2020/22496A. In the structural formula of the following chiral agent Ch-2, Bu represents an n-butyl group.

| Composition E-2 | |
|---|---|
| A liquid crystal compound A-9 | 100.00 parts by mass |
| The following polymerization initiator PI-1 | 3.00 parts by mass |
| The following chiral agent Ch-1 | 4.40 parts by mass |
| The following chiral agent Ch-2 | 1.00 part by mass |
| Methyl ethyl ketone | 201.31 parts by mass |

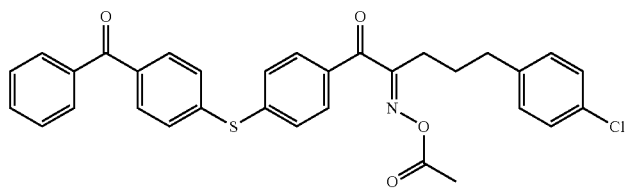

PI-1

-continued

Composition E-2

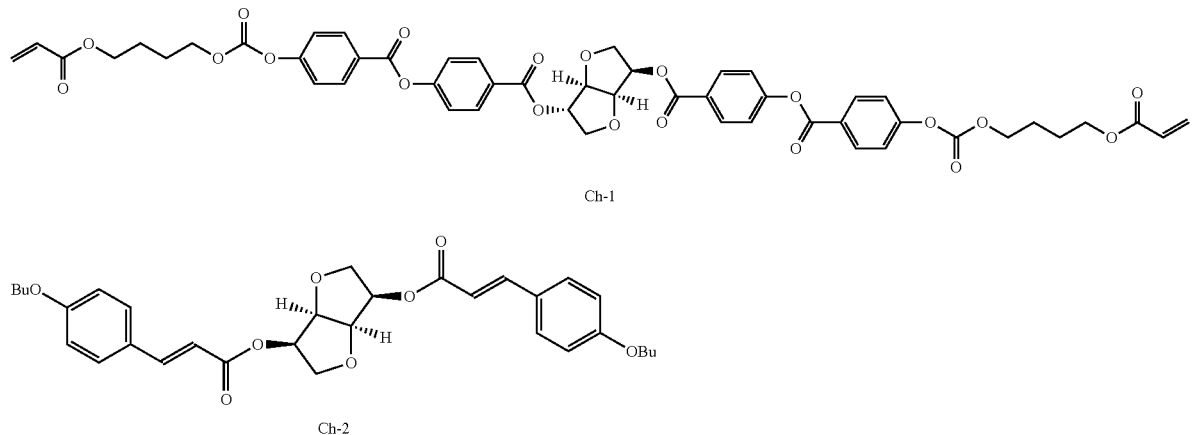

Ch-1

Ch-2

The alignment film P-1 was produced in the same manner as in the above-described "Preparation of support and saponification treatment of support", "Formation of undercoat layer", "Formation of alignment film", and "Exposure of alignment film" in Example 20.

A cholesteric liquid crystal layer was formed by subjecting the alignment film P-1 to multilayer coating with the composition E-2 until the film thickness became 3.5 µm. Here, the multilayer coating refers to the repetition of the process of producing a liquid crystal immobilized layer by applying the composition E-2 for a first layer onto the alignment film, followed by heating and then curing with an ultraviolet ray; and then subjecting the liquid crystal immobilized layers to repeat coating for second and subsequent layers, followed by the same heating and then curing with an ultraviolet ray as described above. Due to the formation by the multilayer coating, the alignment direction of the alignment film is reflected over the upper surface of the liquid crystal layer from the lower surface even in a case where the total thickness of the liquid crystal layer is increased.

As the optically anisotropic layer for the first layer, the composition E-2 was applied onto the alignment film P-1 at 1,000 rotations per minute (rpm) using a spin coater. The coating film was heated using a hot plate at 50° C. for 3 minutes and was further irradiated at 80° C. with ultraviolet rays having a wavelength of 365 nm at an irradiation dose of 300 mJ/cm$^2$ using a high-pressure mercury lamp in a nitrogen atmosphere. As a result, the alignment of the liquid crystal compound was immobilized.

This liquid crystal layer was subjected to repeat coating for the second and subsequent liquid crystal layers, followed by heating and then curing with an ultraviolet ray under the same conditions as described above to form a cholesteric liquid crystal layer.

The formed cholesteric liquid crystal layer was bonded to a light guide plate (a glass having a refractive index of 1.80 and a thickness of 0.50 mm) to produce a light guide element.

The light having a wavelength of 532 nm was incident in the normal direction from the light guide plate side of the produced light guide element. As a result of the above, it was confirmed that the incident light was reflected in the cholesteric liquid crystal layer beyond the critical angle in a direction different from the specular reflection direction and guided in the light guide plate.

Liquid Crystallinity of Composition

When the composition E-2 was dried and the solvent (methyl ethyl ketone) was volatilized, it was confirmed that liquid crystallinity was exhibited.

TABLE 1

| | Compound | Liquid crystallinity | Δn | Solubility | Durability | Light resistance |
|---|---|---|---|---|---|---|
| Example 1 | A-1 | B | A | A | B | A |
| Example 2 | A-3 | A | A | A | A | A |
| Example 3 | A-4 | A | A | A | A | B |
| Example 4 | A-5 | B | A | A | A | A |
| Example 5 | A-6 | A | A | A | A | A |
| Example 6 | A-7 | A | A | A | A | A |
| Example 7 | A-8 | A | A | A | A | A |
| Example 8 | A-9 | A | A | A | A | A |
| Example 9 | A-10 | A | A | A | A | A |
| Example 10 | A-11 | A | A | A | A | A |
| Example 11 | A-12 | A | A | A | A | A |
| Example 12 | A-13 | A | B | A | B | A |
| Example 13 | A-14 | A | A | B | A | A |
| Example 14 | A-15 | A | A | B | B | A |
| Example 15 | A-16 | A | A | A | A | B |
| Example 16 | A-17 | B | A | A | A | A |
| Example 17 | A-18 | A | A | A | A | A |
| Example 18 | A-19 | A | A | A | A | A |

TABLE 1-continued

| | Compound | Liquid crystallinity | Δn | Solubility | Durability | Light resistance |
|---|---|---|---|---|---|---|
| Example 19 | A-20 | A | A | A | A | A |
| Comparative Example 1 | RA-1 | A | D | B | A | B |
| Comparative Example 2 | RA-2 | A | C | B | A | B |

From the results shown in Table 1 above, it was found that the compound represented by General Formula (I) has a high refractive index anisotropy Δn (Examples 1 to 19).

In particular, it was found that from the comparison between Example 12 and the other Examples, in a case where at least two of the plurality of $X^1$'s and the plurality of $X^2$'s in General Formula (I) represent —S—, the refractive index anisotropy Δn is further increased.

In addition, as described above, in a case where the optical element produced by using the composition containing the compound represented by General Formula (I) is used, a high diffraction efficiency can be obtained.

Further, as described above, it is possible to produce a light guide element by using the composition containing the compound represented by General Formula (I) and a chiral agent.

On the other hand, it was found that the refractive index anisotropy Δn of the comparative compound which is not the compound represented by General Formula (I) is low as compared with the compound represented by General Formula (I) (Comparative Examples 1 and 2).

What is claimed is:

1. A compound represented by the following General Formula

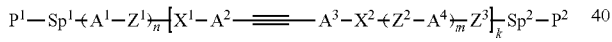

(I)

wherein, in the General Formula (I),
$P^1$ and $P^2$ each independently represent a hydrogen atom, —CN, —NCS, or a polymerizable group,
$Sp^1$ and $Sp^2$ each independently represent a single bond or a divalent linking group,
$Sp^1$ and $Sp^2$ do not represent a divalent linking group containing at least one group selected from the group consisting of an aromatic hydrocarbon ring group, an aromatic heterocyclic group, and an aliphatic hydrocarbon ring group,
$Z^1$, $Z^2$ and $Z^3$ each independently represent a single bond, —O—, —S—, —CHR—, —CHRCHR—, —OCHR—, —CHRO—, —SO—, —SO$_2$—, —COO—, —OCO—, —CO—S—, —S—CO—, —O—CO—O—, —CO—NR—, —NR—CO—, —SCHR—, —CHRS—, —SO—CHR—, —CHR—SO—, —SO$_2$—CHR—, —CHR—SO$_2$—, —CF$_2$O—, —OCF$_2$—, —CF$_2$S—, —SCF$_2$—, —OCHRCHRO—, —SCHRCHRS—, —SO—CHRCHR—SO—, —SO$_2$—CHRCHR—SO$_2$—, —CH—CH—COO—, —CH—CH—OCO—, —COO—CH—CH—, —OCO—CH=CH—, —COO—CHRCHR—, —OCO—CHRCHR—, —CHRCHR—COO—, —CHRCHR—OCO—, —COO—CHR—, —OCO—CHR—, —CHR—COO—, —CHR—OCO—, —CR=CR—, —CR=N—, —N=CR—, —N=N—, —CR=N—N=CR—, —CF=CF—, or —C=C—; R represents a hydrogen atom or an alkyl group having 1 to 10 carbon atoms; in a case where a plurality of R's are present, the plurality of R's may be the same or different from each other; in a case where a plurality of $Z^1$'s and a plurality of $Z^2$'s are present, the plurality of $Z^1$'s and the plurality of $Z^2$'s may be respectively the same or different from each other; a plurality of $Z^3$'s may be the same or different from each other, $Z^3$ linked to $Sp^2$ represents a single bond,
$X^1$ and $X^2$ each independently represent a single bond or —S—, a plurality of $X^1$'s and a plurality of $X^2$'s may be respectively the same or different from each other, at least two of the plurality of $X^1$'s and the plurality of $X^2$'s in the General Formula (I) represent —S—
k represents an integer of 2 to 4, m and n each independently represent an integer of 0 to 3, a plurality of m's may be the same or different from each other,
$A^1$, $A^2$, $A^3$, and $A^4$ each independently represent a group represented by any of the following General Formulae (B-1) to (B-7) or a group formed by linking two or three groups represented by any of the General Formulae (B-1) to (B-7); a plurality of $A^2$'s and a plurality of $A^3$'s may be respectively the same or different from each other; and in a case where a plurality of $A^1$'s and a plurality of $A^4$'s are present, the plurality of $A^1$'s and the plurality of $A^4$'s may be respectively the same or different from each other,

(B-1)

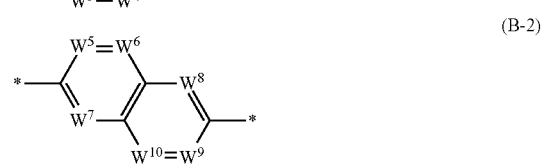

(B-2)

(B-3)

(B-4)

(B-5)

-continued

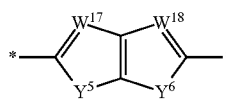
(B-6)

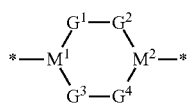
(B-7)

wherein, in the General Formulae (B-1) to (B-7),
$W^1$ to $W^{18}$ each independently represent $CR^1$ or N, $R^1$ represents a hydrogen atom or the following substituent L,
$Y^1$ to $Y^6$ each independently represent $NR^2$, O, or S, $R^2$ represents a hydrogen atom or the following substituent L,
$G^1$ to $G^4$ each independently represent $CR^3R^4$, $NR^5$, O, or S, $R^3$ to $R^5$ each independently represent a hydrogen atom or the following substituent L,
$M^1$ and $M^2$ each independently represent $CR^6$ or N, $R^6$ represents a hydrogen atom or the following substituent L,
* represents a bonding position,
the substituent L is an alkyl group having 1 to 10 carbon atoms, an alkoxy group having 1 to 10 carbon atoms, an alkylamino group having 1 to 10 carbon atoms, an alkylthio group having 1 to 10 carbon atoms, an alkanoyl group having 1 to 10 carbon atoms, an alkanoyloxy group having 1 to 10 carbon atoms, an alkanoylamino group having 1 to 10 carbon atoms, an alkanoylthio group having 1 to 10 carbon atoms, an alkyloxycarbonyl group having 2 to 10 carbon atoms, an alkylaminocarbonyl group having 2 to 10 carbon atoms, an alkylthiocarbonyl group having 2 to 10 carbon atoms, a hydroxy group, an amino group, a mercapto group, a carboxy group, a sulfo group, an amide group, a cyano group, a nitro group, a halogen atom, or a polymerizable group; in a case where the above group described as the substituent L has —CH$_2$—, a group formed by replacing at least one —CH$_2$— contained in the above group with —O—, —CO—, —CH═CH—, or —C≡C— is also included in the substituent L; and in a case where the above group described as the substituent L has a hydrogen atom, a group formed by replacing at least one of hydrogen atoms contained in the above group with at least one selected from the group consisting of a fluorine atom and a polymerizable group is also included in the substituent L.

2. The compound according to claim 1,
wherein n and m in the General Formula (I) represent 0.

3. The compound according to claim 1,
wherein k in the General Formula (I) represents 2.

4. The compound according to claim 1,
wherein, in the General Formula (I), n represents 0; m represents 0 or 1, m at a position closest to $Sp^2$ represents 0; in a case where $X^1$ linked to $Sp^1$ is denoted by $X^{1A}$ and $X^2$ linked to $Z^3$ linked to $Sp^2$ is denoted by $X^{2A}$, at least one of $X^{1A}$ or $X^{2A}$ represents —S—, $X^1$ other than $X^{1A}$ and $X^2$ other than $X^{2A}$ represent a single bond; $Z^2$ and $Z^3$ each independently represent a single bond, —O—, —CHR—, —CHRCHR—, —OCHR—, —CHRO—, —SO—, —SO$_2$—, —COO—, —OCO—, —CO—S—, —S—CO—, —O—CO—O—, —CO—NR—, —NR—CO—, —SO—CHR—, —CHR—SO—, —SO$_2$—CHR—, —CHR—SO$_2$—, —CF$_2$O—, —OCF$_2$—, —OCHRCHRO—, —SO—CHRCHR—SO—, —SO$_2$—CHRCHR—SO$_2$—, —CH═CH—COO—, —CH═CH—OCO—, —COO—CH═CH—, —OCO—CH═CH—, —COO—CHRCHR—, —OCO—CHRCHR—, ═CHRCHR—COO—, —CHRCHR—OCO—, —COO—CHR—, —OCO—CHR—, —CHR—COO—, —CHR—OCO—, —CR═CR—, —CR═N—, —N═CR—, —N═N—, —CR═N—N═CR—, —CF═CF—, or —C≡C—, $Z^3$ linked to $Sp^2$ represents a single bond; R represents a hydrogen atom or an alkyl group having 1 to 10 carbon atoms; and in a case where a plurality of R's are present, the plurality of R's may be the same or different from each other.

5. The compound according to claim 1,
wherein at least one of $P^1$ or $P^2$ in the General Formula (I) represents a polymerizable group.

6. The compound according to claim 1,
wherein, in the General Formula (I), $P^1$ represents a polymerizable group, n represents 0, and $X^1$ linked to $Sp^1$ represents —S—.

7. The compound according to claim 1,
wherein $A^1$, $A^2$, $A^3$, and $A^4$ in the General Formula (I) each independently represent a group represented by the General Formula (B-1) or (B-2), $W^1$ and $W^2$ in the General Formula (B-1) do not represent N at the same time, $W^3$ and $W^4$ do not represent N at the same time, $W^5$ and $W^6$ in the General Formula (B-2) do not represent N at the same time, and $W^9$ and $W^{10}$ do not represent N at the same time.

8. The compound according to claim 1,
wherein at least one of $A^1$, $A^2$, $A^3$, or $A^4$ in the General Formula (I) has the substituent L.

9. The compound according to claim 1,
wherein $Z^1$, $Z^2$, and $Z^3$ in the General Formula (I) each independently represent a single bond, —CHR—, —CHRCHR—, —OCHR—, —CHRO—, or —OCHRCHRO—, $Z^3$ linked to $Sp^2$ represents a single bond; R represents a hydrogen atom or an alkyl group having 1 to 10 carbon atoms; and in a case where a plurality of R's are present, the plurality of R's may be the same or different from each other.

10. The compound according to claim 1,
wherein the compound represented by the General Formula (I) is a compound represented by the following General Formula (I-2) or (I-3),

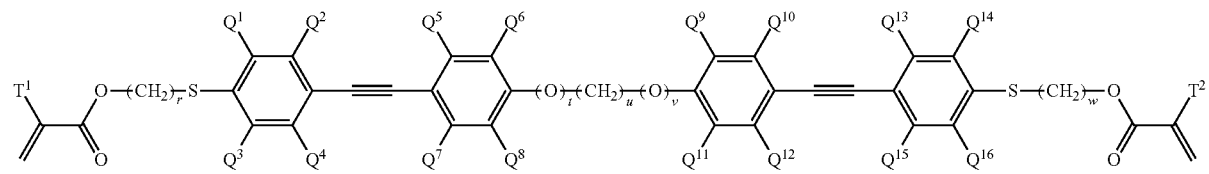
(I-2)

-continued (I-3)
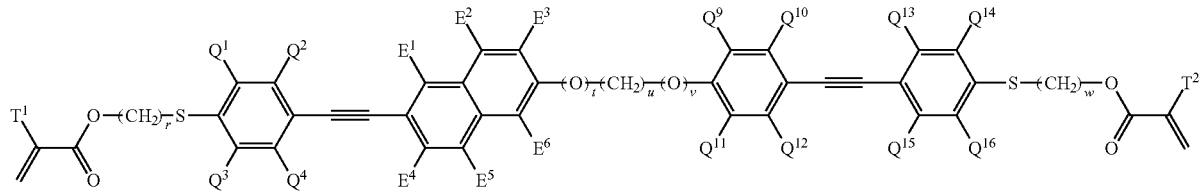

wherein, in the General Formulae (I-2) and (I-3),
$T^1$ and $T^2$ each independently represent a hydrogen atom or a methyl group,
r represents an integer of 1 to 5,
t and v each independently represent 0 or 1,
u represents 1 or 2,
w represents an integer of 1 to 5,
$Q^1$ to $Q^{16}$ each independently represent a hydrogen atom or the substituent L,
$E^1$ to $E^6$ each independently represent a hydrogen atom or the substituent L, and t, u, and v are not simultaneously 1.

11. The compound according to claim 1, wherein the compound has liquid crystallinity.

12. A composition comprising the compound according to claim 1.

13. The composition according to claim 12, further comprising a polymerization initiator.

14. The composition according to claim 12, further comprising a chiral agent.

15. The composition according to claim 12, wherein the composition has liquid crystallinity.

16. The composition according to claim 12, wherein the composition is used for forming an optically anisotropic layer.

17. A cured substance that is obtained by curing the composition according to claim 12.

18. An optically anisotropic body that is obtained by curing the composition according to claim 12.

19. An optical element comprising:
an optically anisotropic layer formed from the composition according to claim 12,
wherein the optically anisotropic layer has an alignment pattern, and
the alignment pattern is an alignment pattern in which an orientation of an optical axis, derived from a compound contained in the composition, continuously changes rotationally along at least one in-plane direction.

20. A light guide element comprising:
the optical element according to claim 19; and
a light guide plate.

* * * * *